(12) United States Patent
Amici et al.

(10) Patent No.: US 8,207,141 B2
(45) Date of Patent: Jun. 26, 2012

(54) PLASMIDS CODING FOR P185$^{neu}$ PROTEIN SEQUENCE VARIANTS AND THERAPEUTIC USES THEREOF

(76) Inventors: Augusto Amici, Camerino (IT); Cristina Marchini, Civitanova Marche (IT); Elena Quaglino, Turin (IT); Federica Cavallo, Cirie' (IT); Guido Forni, Turin (IT)

( * ) Notice: Subject to any disclaimer, the term of this patent is extended or adjusted under 35 U.S.C. 154(b) by 0 days.

(21) Appl. No.: 13/173,339

(22) Filed: Jun. 30, 2011

(65) Prior Publication Data

US 2011/0256162 A1   Oct. 20, 2011

Related U.S. Application Data

(62) Division of application No. 11/665,301, filed as application No. PCT/IB2005/003052 on Oct. 13, 2005, now Pat. No. 7,985,582.

(30) Foreign Application Priority Data

Oct. 15, 2004  (IT) ............................... MI2004A1965

(51) Int. Cl.
*A61K 48/00*      (2006.01)
*C12N 5/00*       (2006.01)
*C12N 15/00*      (2006.01)
*C07H 21/02*      (2006.01)
*C07K 1/00*       (2006.01)

(52) U.S. Cl. .................... 514/44 R; 424/93.2; 435/69.1; 435/325; 435/455; 536/23.1; 536/23.4; 530/350; 530/351

(58) Field of Classification Search ........................ None
See application file for complete search history.

(56) References Cited

OTHER PUBLICATIONS

Raper, Surgery, 137(5):487-492, 2005.*
Kimmelman, BMJ, 220:79-82, 2003.*
Juengst, BMJ, 326:1410-1411, 2003.*
Wolf, Nat. Biotechnol. 20:768-769, 2002.*
Jacob et al., "Combining Human and Rat Sequences in Her-2 DNA Vaccines Blunts Immune Tolerance and Drives Antitumor Immunity", Cancer Res 70(1):119-28 (2010).

* cited by examiner

*Primary Examiner* — Sumesh Kaushal
(74) *Attorney, Agent, or Firm* — Porzio, Bromberg & Newman, P.C.

(57) ABSTRACT

DNA plasmids containing sequences coding for different fragments of 185$^{neu}$ oncoprotein which are able to induce an immune response against p185$^{neu}$-overexpressing tumors, and pharmaceutical compositions thereof are described.

8 Claims, 14 Drawing Sheets

PLASMIDS CODING FOR P185$^{neu}$ PROTEIN SEQUENCE VARIANTS AND THERAPEUTIC USES THEREOF

CROSS-REFERENCE TO RELATED APPLICATION

This application is a divisional of U.S. patent application Ser. No. 11/665,301 filed May 11, 2009, now U.S. Pat. No. 7,985,582, which is a National Stage of International Application No. PCT/IB2005/003052, filed 13 Oct. 2005, which claims the benefit of Application No. MI2004A001965, filed in Italy on 15 Oct. 2004, the disclosures of which Applications are incorporated by reference into this application.

The present invention refers to plasmid vectors containing DNA sequences coding for truncated and chimeric forms of p185$^{neu}$ protein, and use thereof in DNA vaccination against Her-2/neu (ErbB-2)-positive tumors that express p185$^{neu}$ protein. Plasmids according to the invention are capable of eliciting a protective immune response which is based on antibody and/or T lymphocyte induction against p185$^{neu}$ protein-expressing tumors. The invention further refers to pharmaceutical compositions containing such plasmids and use thereof in preventive or therapeutic treatment of p185$^{neu}$-positive tumors.

BACKGROUND OF THE INVENTION

Neoplastic cells often differ from normal cells in that they express several proteins abnormally. Due to this anomalous expression, some proteins can act as Tumor Associate Antigens (TAA). This is because the host immune system can recognize these abnormalities and elicit an immune response that might protect the host from tumor onset and development. To be a target of antitumoral immunotherapy, a TAA must:

- have a pathogenetic role in a certain stage of neoplastic growth;
- be detectable by immune system even when the tumor gives rise to clonal variants which no more express major histocompatibility complex (HLA) glycoproteins;
- be recognized by both antibodies and T lymphocytes.

Several TAA have been discovered in human carcinomas in recent years. Among them, p185$^{neu}$, the protein product of Her-2/neu (ErbB2) oncogene, is a particularly suited target for immunotherapy (Lollini and Forni, 2003, Trends Immunol. 24: 62). p185$^{neu}$ is a membrane receptor of class I receptor tyrosin kinase family, which also encompasses the epidermal growth factor receptor (EGF-R or ErbB-1) and other related receptors (ErbB-3, ErbB-4) which play a key role in cell proliferation and differentiation (Hynes and Stern, 1994, BBA 1198: 165).

p185$^{neu}$ receptor protein can be subdivided into three domains: the extracellular domain (EC domain), the transmembrane domain (TM domain), and the intracytoplasmic domain (IC domain). Recently, the EC domain crystallographic structure of human and rat p185$^{neu}$ protein has been published. This domain has been described to be composed of four subdomains (I/L1, II/CR1, III/L2, and IV/CR2) for approximately 630 amino acids in all. It has been further shown that p185$^{neu}$ protein has a rigid conformation, which allows it to interact with other ErbB receptors, dimerize, and induce transduction of proliferation signal even if this protein binds no ligands directly (Cho et al., 2003, Nature 421: 756).

Her-2/neu (ErbB2) oncogene is involved in normal processes of embryonic organogenesis and epithelial growth, while in adults it is expressed only at faint levels (Press et al., 1990, Oncogene 5: 953). In humans, overexpression of this oncogene is mainly caused by gene amplification. Her-2/neu (ErbB2) oncogene is overexpressed in about 30% of mammary carcinomas, and such an overexpression is related to a more rapid tumor progression (Slamon et al., 1989, Science 244: 707). Among the different strategies which have been proposed, DNA vaccination seems to be an effective method to elicit an immune response to Her-2/neu-positive tumors. Even though p185$^{neu}$ protein is a "self" antigen, i.e. a protein which is normally present in the body, patients with p185$^{neu}$-positive mammary carcinomas often exhibit an immune response, both cellular and humoral (Signoretti et al., 2000, J. Natl. Cancer Inst. 23: 1918; Disis et al., 1994, Cancer Res. 54: 16; Peoples et al., 1995, Proc. Natl. Acad. Sci. USA 92: 432). One of the objectives of antitumoral immunotherapies directed towards p185$^{neu}$ protein is to increase the response intensity in patients with a pre-existing immune response, or to generate an immune response in patients in whom this response is undetectable. The fact that p185$^{neu}$ protein is a "self" antigen entails that the vaccine must be able to overcome an immunotolerant state.

The inventors of the instant patent application were the first using and validating the efficacy of DNA vaccination in eliciting an immune protection both to spontaneous mammary carcinomas and transplantable Her-2/neu-positive tumors. These studies have proven that prevention and treatment of preneoplastic lesions is an accessible goal. In particular, in experiments aimed at preventing the development of spontaneous mammary tumors that arise in transgenic mice due to rat Her-2/neu oncogene (FVB/neuT mice and BALB-neuT mice), it has been shown that the plasmid coding for rat p185$^{neu}$ protein EC and TM domains is capable of eliciting a more effective protection compared to the plasmid coding for full-length p185$^{neu}$ protein or plasmid coding for its EC domain only (secreted antigen) (Amici et al., 2000, Gene Ther. 7: 703; Rovero et al., 2000, J. Immunol. 165: 5133). Similar data have been reported by Chen et al., (1998, Cancer Res. 58: 1965). Furthermore, it has been shown that efficacy of vaccination with DNA plasmids is strongly increased if it is followed by a very short electric pulse when plasmids are inoculated intramuscularly (Quaglino et al., 2004, Cancer Res. 64: 2858). Other authors have shown that plasmids coding for full-length p185$^{neu}$ protein, if necessary mutated such that it does not possess tyrosine kinase activity, are efficacious in preventing the onset of tumors following the transplant of p185$^{neu}$-positive cancer cells (Wei-Zen et al., 1999, Int. J. Cancer 81: 748). The same plasmids have proven as much effective even when, deprived of the leader signal responsible for protein processing in the endoplasmic reticulum, they bring about the cytoplasmic localization of p185$^{neu}$ antigen. When plasmids coding for p185$^{neu}$ protein which localizes in membrane thanks to the presence of a leader signal are used, protections depends upon an immune response which relies on antibodies. On the contrary, a T lymphocyte-mediated immune response is observed if vaccine does not contain a leader signal, and hence p185$^{neu}$ protein localizes in the cytoplasm of transfected cells rather than on their plasma membrane (Pilon et al., 2001, J. Immunol. 167: 3201). In addition, a combined vaccination obtained by using both plasmids with a leader signal and those in which this leader signal has been deleted, is more effective in protecting against tumor growth (Piechocki et al., 2001, J. Immunol. 167: 3367). This demonstrates that there is a synergistic effect between humoral and cellular responses in the prevention of p185$^{neu}$-positive carcinomas (Reilly et al., 2001, Cancer Res. 61: 880).

Vaccination with the plasmid coding for EC and TM domains (EC-TM plasmid) has proven efficacious not only in preventing the development of spontaneous p185$^{neu}$-positive carcinomas, but also in treating tumor masses of 2 mm in diameter by involving a range of effector immune system mechanisms (T helper and T killer cells, antibodies, macrophages, neutrophils, natural killer cells, Fc receptors, IFN-gamma, and perforins), which coordinately contribute to tumor rejection (Curcio et al., 2003, *J. Clin. Invest.* 111: 1161).

DESCRIPTION OF THE INVENTION

Figure 1:
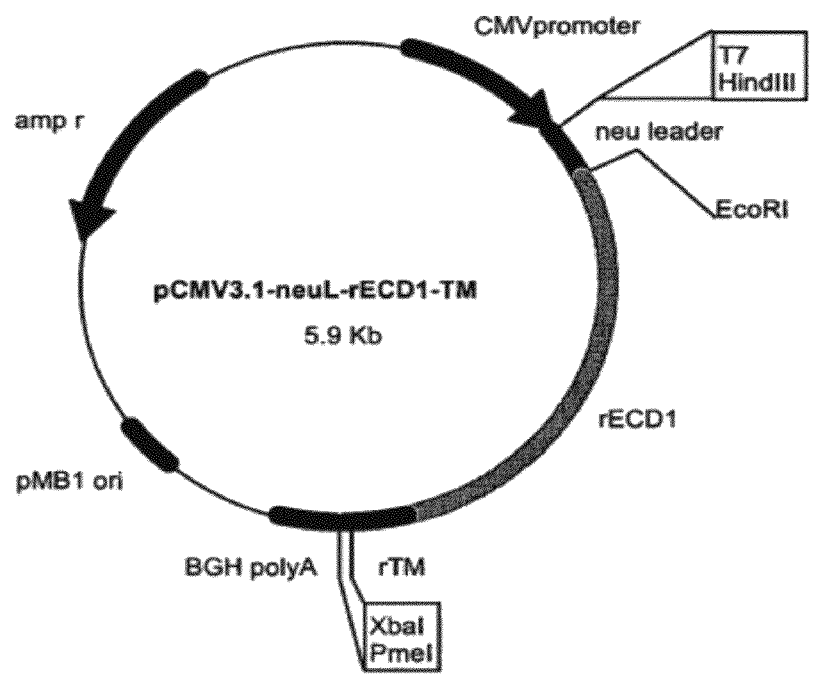
FIG. 1 is a schematic diagram of the construction of plasmid pCMV3.1-neuL-rEC1-TM (−70 amino acids).

Several plasmids coding for the full-length TM domain and decreasing portions of EC domain of rat p185$^{neu}$ protein have been constructed. The truncated plasmids, obtained by deleting the NH$_2$-terminal 240 base pairs (bp), or multiples of this length, were used in experiments aimed at preventing growth of transplantable rat p185$^{neu}$ protein-overexpressing tumor cells (TUBO cells). Furthermore, a series of plasmids coding for chimeric p185$^{neu}$ protein forms were created by adding NH$_2$-terminal portions of human ErbB2 cDNA to sequences coding for the truncated forms of rat protein to reconstitute the whole protein sequence.

Protection achieved following vaccination with plasmid coding for the full-length EC and TM domains is mainly due to antibody production, while protection attained by using plasmids coding for the truncated forms of rat p185$^{neu}$ protein is not associated with a significant antibody production in many cases.

On the basis of the results of the in vivo experiments, plasmids capable of inducing a strong immune response, both antibody and T lymphocyte-mediated, were selected.

In a first aspect, the invention refers to plasmids containing a coding sequence for a p185$^{neu}$ protein fragment, which sequence is selected from the group consisting of SEQ ID NO: 1-5; or a sequence coding for a chimeric p185$^{neu}$ protein, which sequence is selected from the group consisting of SEQ ID NO:6-12 (reference sequences for genes coding for human and rat p185$^{neu}$ proteins are deposited in Gene Bank with accession NO. M11730 and X03362, respectively).

DNA sequences coding for the truncated and chimeric forms of p185$^{neu}$ protein according to the invention can be inserted into any plasmid vectors suitable for use in mammals, particularly in humans. Besides the above coding sequences, plasmids can include functional elements to control transcription, in particular promoters, preferably the CMV promoter, located upstream of the coding sequence, transcription initiation and stop sequences; a selection marker, preferably the ampicilline or kanamycine resistance genes; CpG motifs; a polyadenilation site; and in case enhancers or transcription activators. The elements for controlling transcription must be suitable for use of vectors in mammals, particularly in humans.

In another aspect, the invention concerns a pharmaceutical composition containing a DNA plasmid defined as above, together with pharmaceutically acceptable vehicles and excipients. Alternatively, the compositions can contain admixtures of two or more different plasmids coding for both the truncated and chimeric forms of p185$^{neu}$ protein. The pharmaceutical compositions in a suitable form for parenteral administration, preferably in the form of an injectable solution, are preferably used for DNA vaccination. Principles and methods for DNA vaccination are known to those skilled in the art, and are described, e.g., in Liu, 2003; *J. Int. Med.* 253: 402.

Utilization of plasmids coding for the p185$^{neu}$ truncated and chimeric forms to preventively and therapeutically vaccinate against p185$^{neu}$-positive (Her-2/neu-, ErbB-2-positive) tumors has a variety of advantages which ameliorate its efficacy. For plasmids coding for the truncated forms, these advantages are:

1) The possibility to obtain a vaccine coding only for definite TAA portions against which it is desired to develop an immune response; this vaccine has a less chance to elicit autoimmune phenomena.
2) The exclusive induction of some selected forms of immune response, i.e. an antibody-mediated form or a T lymphocyte-mediated form.
3) The possibility to produce vaccines which combine multiple epitopes having a defined immunogenicity by binding cDNA fragments each other which code for different truncated forms, not necessarily sequentially.

The use of chimeric plasmids generated by a combination of truncated forms of p185$^{neu}$ from a different animal species allows to:

a) Vaccinate with plasmids coding for protein determinants of the same species to be immunized, e.g. humans, which is able to elicit a specific high-affinity response;
b) Combine plasmids coding for antigenic determinants of the same species to be immunized with cDNA sequences coding for antigenic determinants from other species, the antigenic determinants showing a substantial similarity but differing in that those from other species elicit a more intense immune response, thus overcoming the tolerance state. These allogeneic determinants, which are recognized as partially exogenous, act as helper determinants facilitating the induction of a more intense response and cytokine release;
c) Combine plasmids coding for antigenic determinants of the same species with cDNA sequences which, by coding determinants of another species, in some individuals can give rise to heteroclytic determinants which bind with higher affinity to HLA molecules and induce more intense immune responses having a higher affinity;

d) Have a vaccine which combines advantages from a) with those from b) and c).

Properly formulated DNA plasmids according to the invention are used in preventive or therapeutic treatment of humans or animals which show a high risk of developing p185$^{neu}$-positive carcinomas, or patients carrying p185$^{neu}$-positive primary tumors, their relapses or metastases. Prevention can be primary, when the tumor is not evident yet; secondary, when the tumor is in its initial stages as a preneoplastic lesion; or tertiary, if a tumor relapse or metastatic process is observed.

Tumors treatable with plasmids or compositions of the invention are primarily those of epithelial origin, particularly pulmonary, ovarian, and mammary adenocarcinomas; squamous head and neck carcinomas, and more generally p185$^{neu}$ protein-expressing tumors.

DETAILED DESCRIPTION OF THE INVENTION

Figure 2:
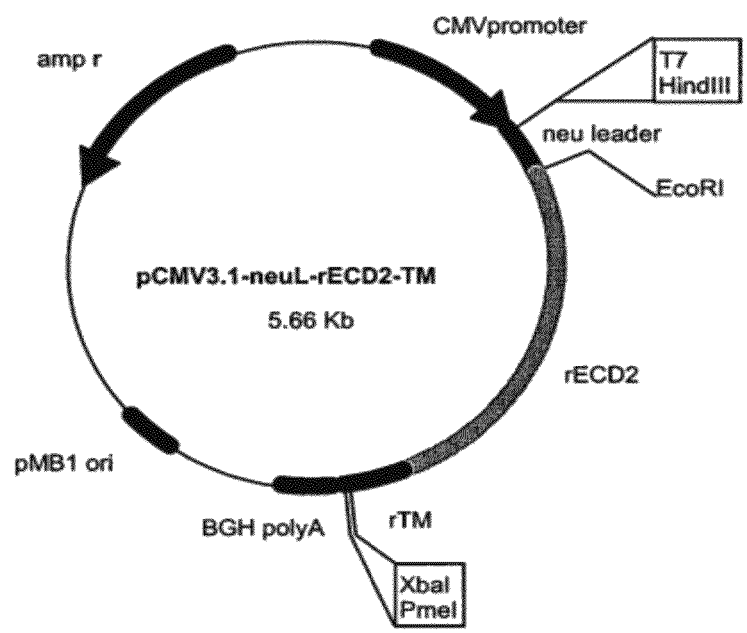
FIG. 2 is a schematic diagram of the construction of plasmid pCMV3.1-neuL-rEC2-TM (−150 amino acids).
Figure 3:
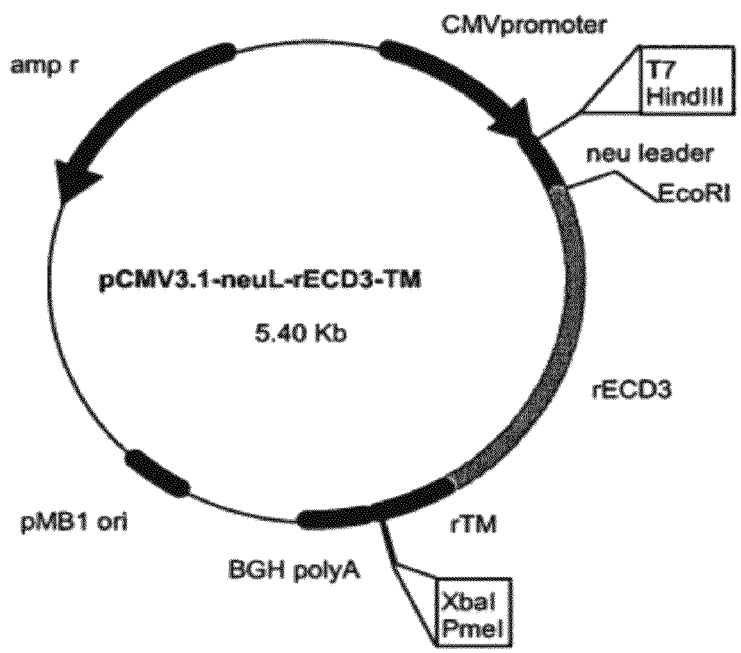
FIG. 3 is a schematic diagram of the construction of plasmid pCMV3.1-neuL-rEC3-TM (−230 amino acids).
Figure 4:
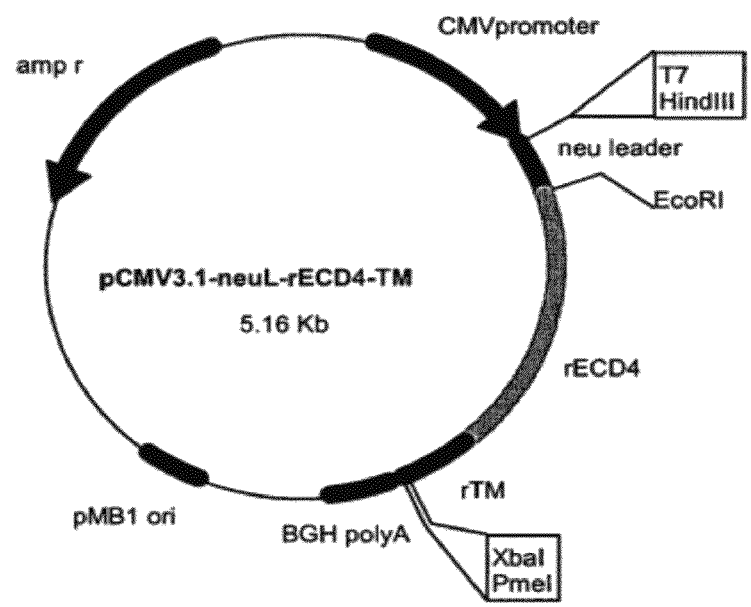
FIG. 4 is a schematic diagram of the construction of plasmid pCMV3.1-neuL-rEC4-TM (−310 amino acids).
Figure 5:
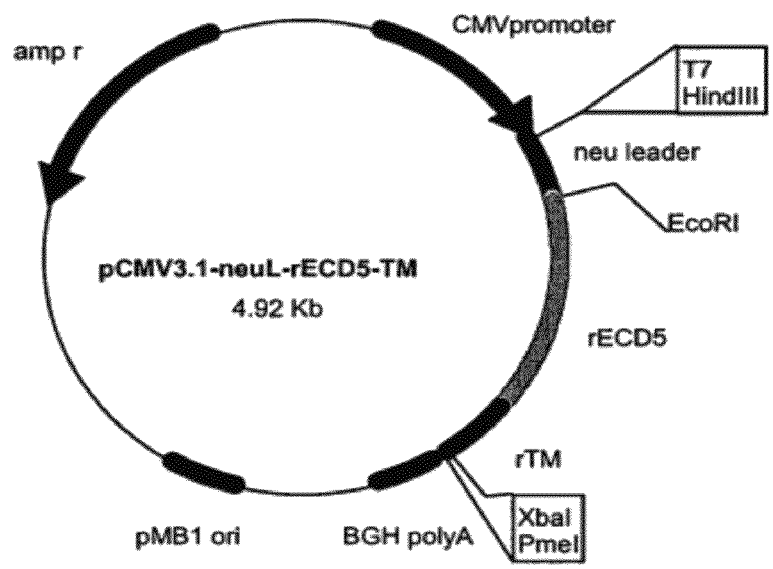
FIG. 5 is a schematic diagram of the construction of plasmid pCMV3.1-neuL-rEC5-TM (−390 amino acids).
Figure 6:
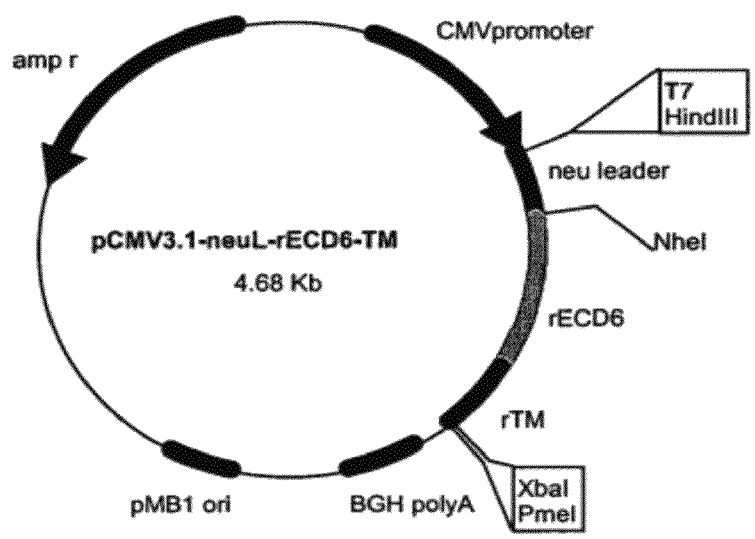
FIG. 6 is a schematic diagram of the construction of plasmid pCMV3.1-neuL-rEC6-TM (−470 amino acids).
Figure 7:
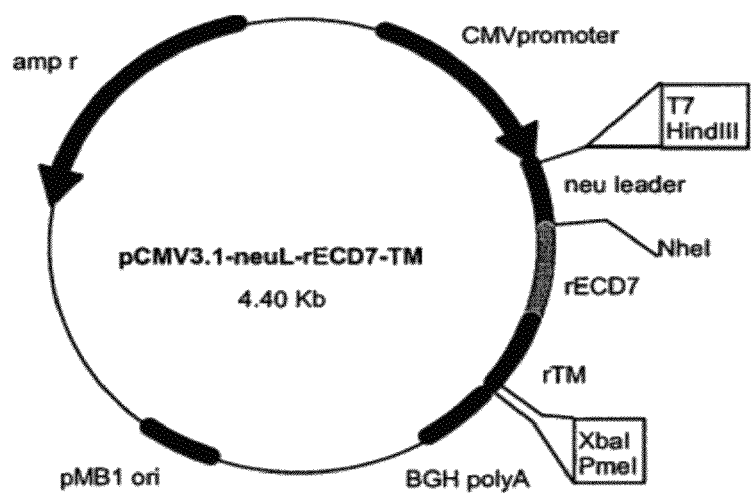
FIG. 7 is a schematic diagram of the construction of plasmid pCMV3.1-neuL-rEC7-TM (−550 amino acids).

Construction of Plasmids Coding for Truncated Forms of Rat p185$^{neu}$ Protein The plasmid backbone pCMV3.1 (obtained in our laboratory starting from pcDNA3.1 from Invitrogen, Milan, Italy) was used to produce the DNA plasmids coding for the full-length TM domain and decreasing portions of EC domain of rat p185$^{neu}$ protein. pCMV3.1 contains the rat Her-2/neu 5' UTR nucleotide sequence (which is transcribed but not translated) and leader sequence (neuL). The secretion signal DNA fragment of rat p185$^{neu}$ protein was obtained by enzymatic amplification of DNA using the pCMV-EC-TM vector (Amici et al., 2000, *Gene Ther.*, 7: 703; Rovero et al., 2000, *J. Immunol.*, 165: 5133) as a template, T7 primer as a sense oligonucleotide (oligonucleotide #1), and an oligonucleotide (oligonucleotide #2) having a terminal EcoRI site as an antisense oligonucleotide. Following purification and digestion with HindIII and EcoRI restriction enzymes, the amplified fragment was cloned into pCMV3.1 plasmid which had been digested with the same enzymes, thus obtaining pCMV3.1-neuL. Subsequently, seven different sequences coding for the deleted fragments of EC domain and full-length TM domain of rat p185$^{neu}$ protein have been inserted in frame into pCMV3.1-neuL vector digested with EcoRI and XbaI restriction enzymes. The new plasmids so obtained were designated pCMV3.1-neuL-rEC1-TM (−70 amino acids) (FIG. 1), pCMV3.1-neuL-rEC2-TM (−150 amino acids) (FIG. 2), pCMV3.1-neuL-rEC3-TM (−230 amino acids) (FIG. 3), pCMV3.1-neuL-rEC4-TM (−310 amino acids) (FIG. 4), pCMV3.1-neuL-rEC5-TM (−390 amino acids) (FIG. 5), pCMV3.1-neuL-rEC6-TM (−470 amino acids) (FIG. 6), and pCMV3.1-neuL-rEC7-TM (−550 amino acids) (FIG. 7). The fragment coded for by the first of these plasmids is 70 amino acids shorter, including the secretion signal amino acid sequence. All other fragments are progressively shorter by 80 amino acids.

These fragments have been produced by enzymatic amplification of DNA using seven different sense oligonucleotides all having a terminal EcoRI restriction site (oligonucleotides #3-#9), and an antisense oligonucleotide (oligonucleotide #10) capable of recognizing a site called "pcDNA3.1/BGH Reverse Priming Site" (830-850 nt) at the 3' end of pCMV3.1 multiple cloning site. As a DNA template for PCR, pCMV-EC-TM vector (Amici A. et al. 2000, *Gene Ther.* 7: 703; Rovero et al., 2000, *J. Immunol.* 165: 5133) was used. Following enzymatic digestion with EcoRI and XbaI restriction enzymes, amplification products were cloned into pCMV3.1-neuL plasmid.

Vaccination with pCMV3.1-neuL-rEC4-TM plasmid as well as vaccination with pCMV3.1-neuL-rEC-TM plasmid which codes for the full-length EC and TM domains protects 100% of BALB/c mice from developing tumors induced by inoculation of TUBO cells. On the other hand, vaccination with pCMV3.1-neuL-rEC 1-TM, pCMV3.1-neuL-rEC2-TM, and pCMV3.1-neuL-rEC3-TM plasmids which code for the first three truncated forms of p185" protein protects 70-80% of BALB/c mice. pCMV3.1-neuL-rEC5-TM plasmid which codes for the fifth truncated form protects 50% of BALB/c mice, while pCMV3.1-neuL-rEC6-TM and pCMV3.1-neuL-rEC7-TM plasmids which code for the sixth and seventh truncated forms induce no protection. The results obtained demonstrate that cellular response activated by the p185$^{neu}$ protein truncated forms whose localization is cytoplasmic, is sufficient in antitumoral prevention. However, concomitant activation of cellular and humoral responses allows obtaining a more effective therapy (Rielly et al., 2001, *Cancer Res.* 61: 880). To attain antibody production, vaccination must be carried out with plasmid coding for the full-length EC and TM domains of p185$^{neu}$ protein. Vaccination with pCMV3.1-neuL-rEC4-TM plasmid which codes for the fourth truncated p185$^{neu}$ form lacking amino acids 1-310 is still able to confer a full protection, but antibody response is 10-fold lower compared to that of pCMV3.1-neuL-rEC-TM plasmid (Table 1).

TABLE 1

| Plasmids | N° mice | Protection | Antibodies |
| --- | --- | --- | --- |
| pCMV3.1-neuL | 5 | 0% | — |
| pCMV3.1-neuL-rEC-TM | 5 | 100% | +++ |
| pCMV3.1-neuL-rEC1-TM | 5 | 80% | — |
| pCMV3.1-neuL-rEC2-TM | 5 | 75% | — |
| pCMV3.1-neuL-rEC3-TM | 5 | 70% | — |
| pCMV3.1-neuL-rEC4-TM | 5 | 100% | + |
| pCMV3.1-neuL-rEC5-TM | 5 | 50% | — |
| pCMV3.1-neuL-rEC6-TM | 5 | 0% | — |
| pCMV3.1-neuL-rEC7-TM | 5 | 0% | — |

Construction of Chimeric Human-Rat Plasmids Capable of Coding for Seven Different Fusion Forms of p185$^{neu}$ Protein (HuRT1-7)

The majority of epitopes presented by HLA are located on the first subdomain (I/L1) of p185$^{neu}$ protein. Therefore, chimeric plasmids coding for sequences of human ErbB2 protein which are increasingly longer starting from NH$_2$-end (the outermost portion of EC domain) have been constructed to induce a specific immune response against these epitopes. These new plasmids, designated HuRT (Human Rat Transmembrane), were created by adding the lacking portions of human ErbB2 cDNA to sequences which code for the truncated forms of rat p185$^{neu}$ protein.

The first five truncated plasmids coding for full-length TM domain and decreasing fragments of EC domain of rat p185$^{neu}$ protein were digested with HindIII and EcoRI restriction enzymes. The five different human cDNA fragments obtained by PCR and digested at their ends were cloned within these five truncated plasmids, so that reading frame was maintained. The cDNA fragments coding for portions of human p185$^{neu}$ protein to be inserted, including the 5' UTR region and secretion signal to pass through endoplasmic reticulum, were produced by amplification using pcDNA3.1erbB2 plasmid as a template. Six oligonucleotides were used as primers. The sense oligonucleotide is the same for all six primers and corresponds to T7 primer (oligonucleotide #1), while the five antisense oligonucleotides were designed so that they recognized human ErbB2 oncogene cDNA in increasingly advanced positions of the sequence and had an EcoRI restriction site at their 3' ends (oligonucleotides #11-#15). Following purification and digestion with HindIII and EcoRI restriction enzymes, the amplified fragments were inserted into corresponding plasmids (pCMV3.1-rEC1-TM, pCMV3.1-rEC2-TM, pCMV3.1-rEC3-TM, pCMV3.1-rEC4-TM, pCMV3.1-rEC5-TM), which had been previously digested with the same restriction enzymes. In this way five new plasmids have been obtained (pCMV3.1-HuRT1-5) which code for chimeric proteins of 689 amino acids in length, 2 amino acids of which (Glu-Phe) belong to the EcoRI restriction site used to join human and rat DNAs. The proteins coded for by these chimeric plasmids differ from each other by increasing portions of human p185$^{neu}$ protein and decreasing portions of rat p185$^{neu}$ protein.

To obtain the chimeric plasmids coding for the sixth and seventh truncated forms of rat p185$^{neu}$ protein, two new plasmids were constructed in which cloning sites other than EcoRI could be used, as an EcoRI restriction site is present in the position 1450 in human ErbB2 gene sequence. pCMV3.1 was modified by using a synthetic sequence made up of a sense oligonucleotide (oligonucleotide #16) and an antisense oligonucleotide (oligonucleotide #17), so that one of the two restriction sites for PmeI enzyme was deleted and the restriction sites for HindIII and NheI restriction enzymes, located on its multiple cloning site, were inverted. The new plasmid backbone so obtained was designated pCMV3.1H/N. Fragments for the sixth and seventh truncated forms of rat p185$^{neu}$ protein were produced by amplification using pCMV-EC-TM plasmid (Amici et al., 2000, *Gene Ther.*, 7: 703; Rovero et al., 2000, *J. Immunol.*, 165: 5133) as a template and two different sense oligonucleotides with a NheI restriction site at their ends (oligonucleotides #18 and #19), and antisense oligonucleotide #10.

Following enzymatic digestion with restriction enzymes NheI and PmeI, the amplification products were cloned into pCMV3.1H/N plasmid, thus obtaining the new pCMV3.1H/N-rEC6-TM and pCMV3.1H/N-rEC7-TM plasmids. The cDNA fragments coding for portions of human p185$^{neu}$ protein to be inserted to generate the chimeric pCMV3.1H/N-HuRT6 and pCMV3.1H/N-HuRT7 plasmids were obtained by amplification using pcDNA3.1erbB2 plasmid as a template, T7 primer as a sense oligonucleotide (oligonucleotide #1), and two primers designed so that they recognized human cDNA at suitable positions and had a NheI restriction site at their ends (oligonucleotides #20 and #21), as antisense oligonucleotides.

Following purification and digestion with HindIII and NheI restriction enzymes, the amplified fragments were inserted into corresponding plasmids (pCMV3.1H/N-rEC6-TM; pCMV3.1H/N-rEC7-TM), which had previously digested with the same restriction enzymes. In this way the two new chimeric pCMV3.1H/N-HuRT6 and pCMV3.1H/N-HuRT7 plasmids were obtained, which code for proteins of 689 amino acids in length, 2 amino acids of which (Val-Ser) belong to the NheI restriction site used to join human and rat DNAs.

Figure 8:
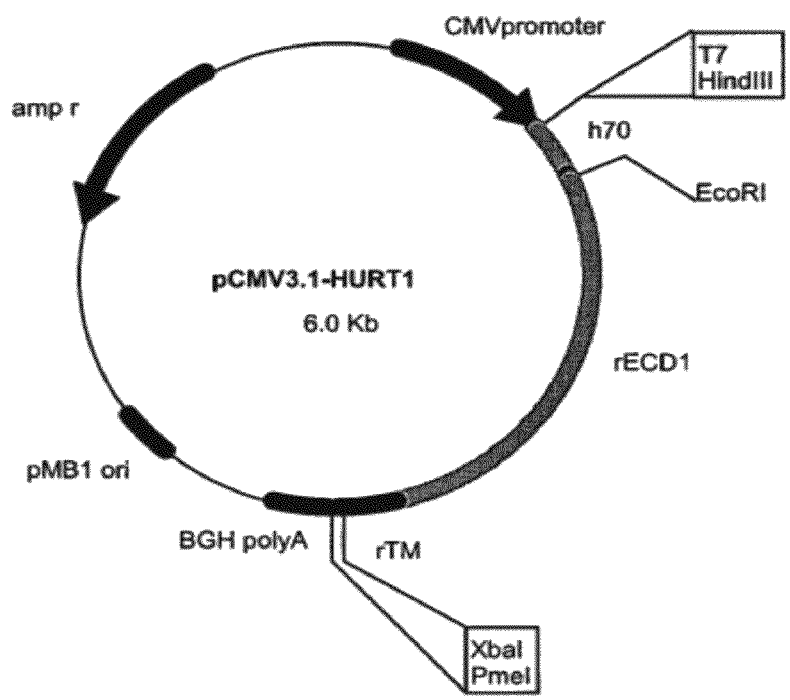
FIG. 8 is a schematic diagram of the construction of plasmid pCMV3.1-HuRT1.
Figure 9:
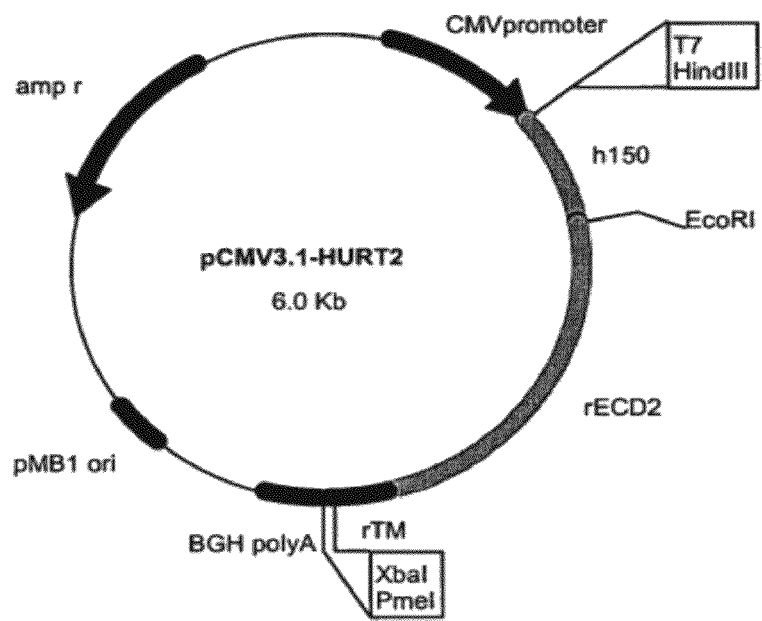
FIG. 9 is a schematic diagram of the construction of plasmid pCMV3.1-HuRT2.
Figure 10:
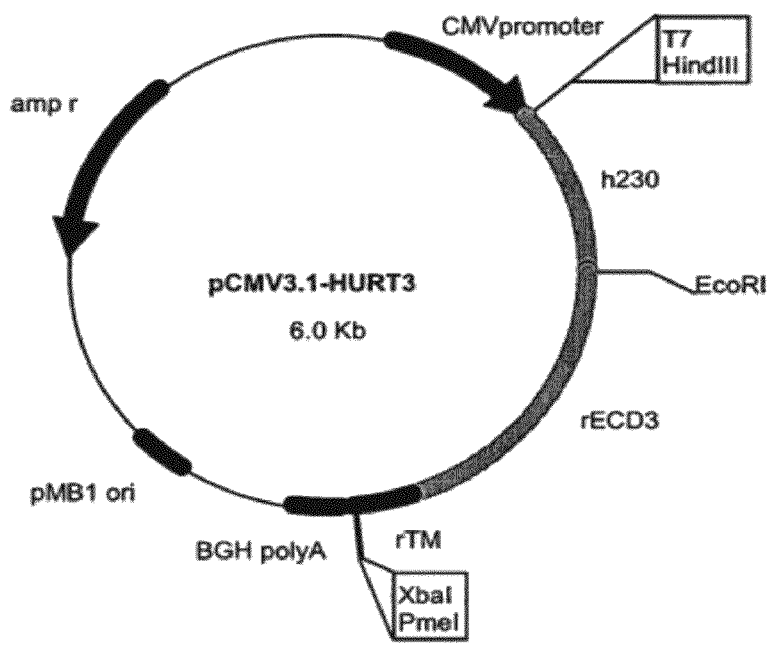
FIG. 10 is a schematic diagram of the construction of plasmid pCMV3.1-HuRT3.
Figure 11:
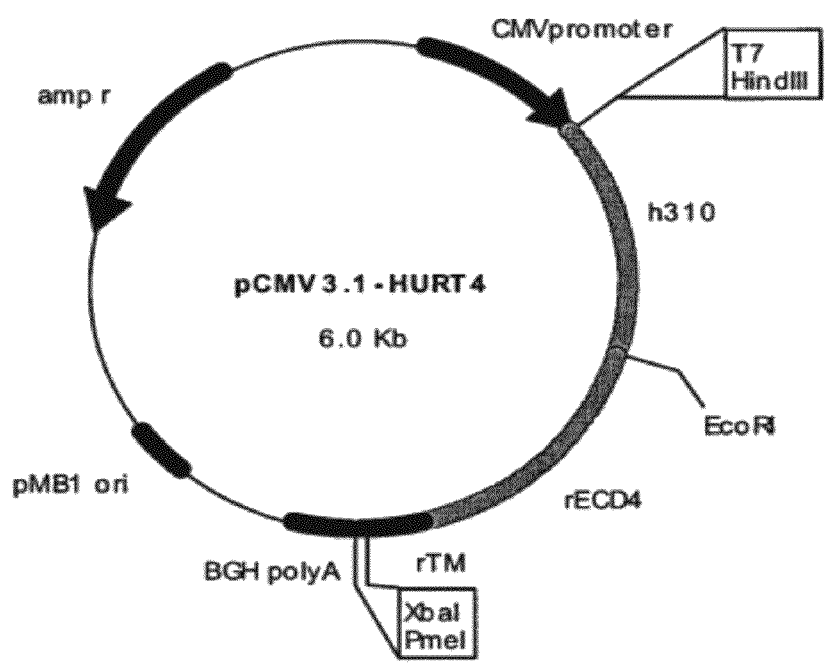
FIG. 11 is a schematic diagram of the construction of plasmid pCMV3.1-HuRT4.
Figure 12:
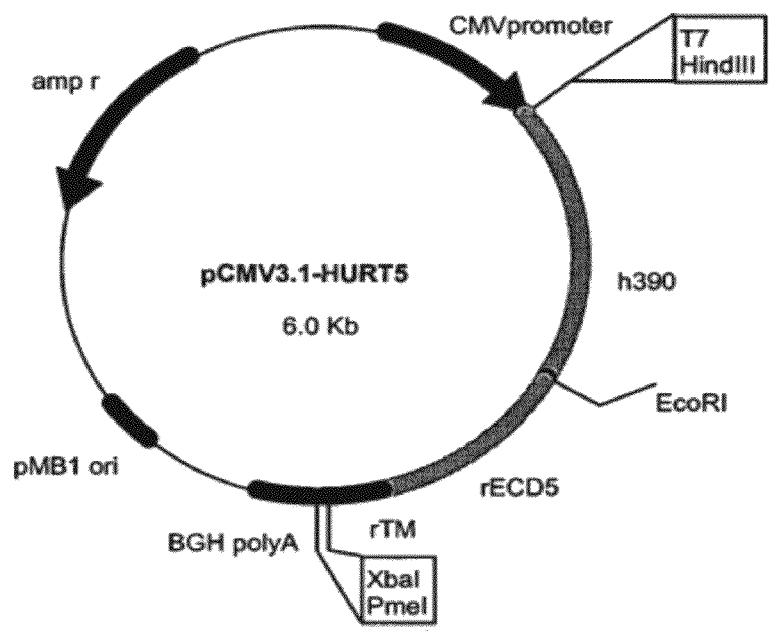
FIG. 12 is a schematic diagram of the construction of plasmid pCMV3.1-HuRT5.
Figure 13:
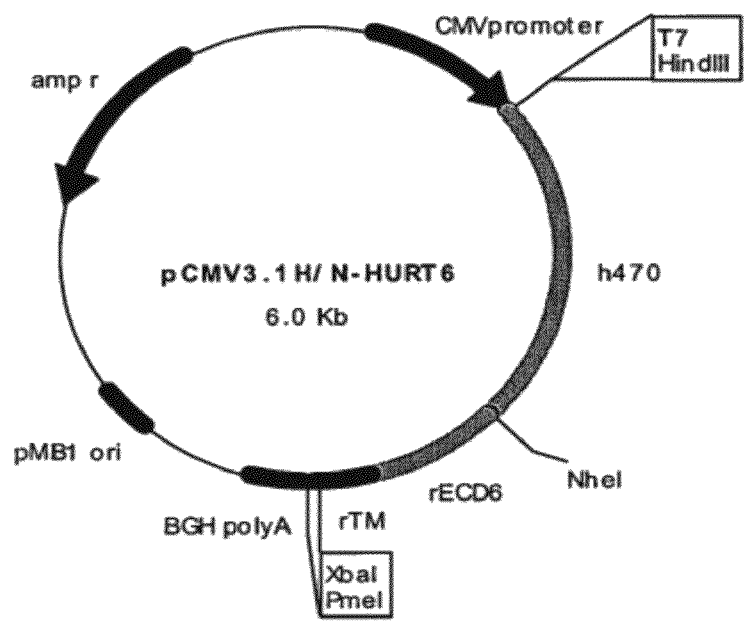
FIG. 13 is a schematic diagram of the construction of plasmid pCMV3.1H/N-HuRT6.
Figure 14:
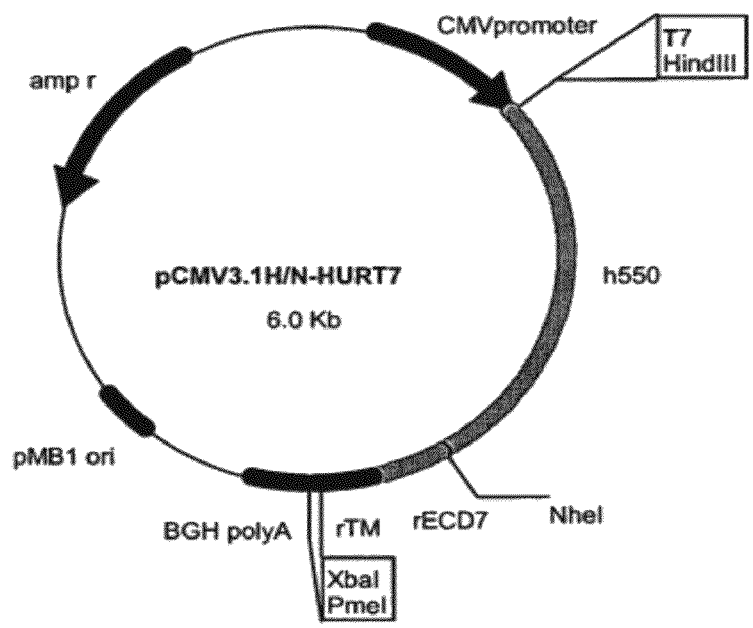
FIG. 14 is a schematic diagram of the construction of plasmid pCMV3.1H/N-HuRT7.

These manipulations led to the following plasmids:
pCMV3.1-HuRT1 plasmid (FIG. 8), which codes for 70 amino acids of EC domain of human p185$^{neu}$ protein, 2 amino acids belonging to EcoRI site and 618 amino acids of rat p185$^{neu}$ protein
pCMV3.1-HuRT2 plasmid (FIG. 9), which codes for 150 amino acids of human p185$^{neu}$ protein EC domain and 538 amino acids of rat p185$^{neu}$ protein
pCMV3.1-HuRT3 plasmid (FIG. 10), which codes for 230 amino acids of EC domain of human p185$^{neu}$ protein and 458 amino acids of rat p185' protein
pCMV3.1-HuRT4 plasmid (FIG. 11), which codes for 310 amino acids of EC domain of human p185$^{neu}$ protein and 378 amino acids of rat p185$^{neu}$ protein
pCMV3.1-HuRT5 plasmid (FIG. 12), which codes for 390 amino acids of EC domain of human p185$^{neu}$ protein and 298 amino acids of rat p185$^{neu}$ protein
pCMV3.1H/N-HuRT6 plasmid (FIG. 13), which codes for 470 amino acids of EC domain of human p185$^{neu}$ protein and 218 amino acids of rat p185$^{neu}$ protein
pCMV3.1H/N-HuRT7 plasmid (FIG. 14), which codes for 550 amino acids of EC domain of human p185$^{neu}$ protein and 138 amino acids of rat p185$^{neu}$ protein.

The indirect evidence of a membrane expression of the chimeric human-rat proteins coded for by these plasmids has been obtained by immunizing mice with the seven new plasmids (pCMV3.1-HuRT1-5 and pCMV3.1H/N-HuRT6-7). The sera from all vaccinated mice have specific antibodies against the chimeric human and rat p185$^{neu}$ protein. Furthermore, animals vaccinated with plasmids coding for the seven different chimeric proteins are protected from a lethal inoculation of TUBO cells and/or human p185$^{neu}$ protein-overexpressing tumor cells (D2F2-E2 cells).

EXAMPLES

Example 1

Construction of pCMV3.1-HuRT5 Plasmid pCMV3.1-rEC5-TM plasmid, which codes for the fifth truncated form of rat p185$^{neu}$ protein, was digested with HindIII and EcoRI restriction enzymes (BioLabs, Beverly, Mass.) to delete the 5' UTR region and neuL sequence.

The 4794 bp DNA band corresponding to pCMV3.1-rEC5-TM plasmid lacking the 5' UTR region and neuL sequence was separated by agarose gel electrophoresis and eluted using a Qiaquick gel extraction kit (Qiagen, Italy). The cDNA for the 5' UTR region, leader sequence, and sequence coding for the missing part of human ErbB2 gene was obtained by PCR. pcDNA3.1ErbB2 plasmid was used as a template, T7 primer (oligonucleotide #1) was used as a sense oligonucleotide, and a primer with an EcoRI restriction site at its 5' end (oligonucleotide #15) was used as an antisense oligonucleotide. To perform the PCR reaction, reagents and a proofreading Taq polymerase of Finnzymes (CELBIO, Milan, Italy) were employed. Following the PCR reaction, the amplified DNA was purified and precipitated by standard methods, resuspended in 50 1 H$_2$O, and digested with HindIII and EcoRI restriction enzymes. The cDNA fragment coding for the relevant portion of human ErbB2 and the linearized pCMV3.1-rEC5-TM plasmid were cloned by ligation reaction using T4 DNA ligase (BioLabs, Beverly, Mass.).

The ligation product was then used to transform DH5 strain *E. coli* bacteria which had been made competent by the calcium chloride technique.

The clones so obtained were analyzed by alcaline lysis to detect the clones containing the chimeric pCMV3.1-HuRT5 plasmid.

pCMV3.1-HuRT5 was then analyzed by the Sanger sequencing method using an ABI PRISM 310 Genetic Analyzer automated sequencer (Applied Biosystem) to verify that insertion of human sequence portion coding for ErbB2 gene into plasmid coding for the fifth truncated form of rat p185$^{neu}$ protein had taken place correctly and without altering the reading frame.

List of Oligonucleotides:
1 T7 primer (SEQ ID No: 13)
2 neu leader antisense EcoRI (SEQ ID No: 14)
3 rECD1 sense EcoRI (SEQ ID No: 15)
4 rECD2 sense EcoRI (SEQ ID No: 16)
5 rECD3 sense EcoRI (SEQ ID No: 17)
6 rECD4 sense EcoRI (SEQ ID No: 18)
7 rECD5 sense EcoRI (SEQ ID No: 19)
8 rECD6 sense EcoRI (SEQ ID No: 20)
9 rECD7 sense EcoRI (SEQ ID No: 21)
10 pcDNA3.1/BGH Reverse priming site (SEQ ID No: 22)
11 His-Myc sense EcoRI mut (SEQ ID No: 23)
12 His-Myc antisense EcoRI (SEQ ID No: 24)
13 70 erbB2 antisense EcoRI (SEQ ID No: 25)
14 150 erbB2 antisense EcoRI (SEQ ID No: 26)
15 230 erbB2 antisense EcoRI (SEQ ID No: 27)
16 310 erbB2 antisense EcoRI (SEQ ID No: 28)
17 390 erbB2 antisense EcoRI (SEQ ID No: 29)
18 HindIII-NheI sense (SEQ ID No: 30)
19 HindIII-NheI antisense (SEQ ID No: 31)
20 rECD6 sense HheI (SEQ ID No: 32)
21 rECD7 sense HheI (SEQ ID No: 33)
22 470 erbB2 antisense HheI (SEQ ID No: 34)
23 550 erbB2 antisense HheI (SEQ ID No: 35)

Example 2

In Vivo Testing

Animals

BALB/c strain female mice about 7-week old were used for all experiments. Animals came from Charles River Laboratories (Calco, Milan, Italy), where they had been bred aseptically and according to the rules established by European Community.

Intramuscular Administration Followed by In Vivo Electroporation

To avoid pain and undesired contractions of tibial muscles, each mouse was anaesthetized by intraperitoneal injection of 300 µl Avertin, a solution consisting of 0.58 g tribromoethanol (Sigma-Aldrich) and 310 µl Tert-Amyl alcohol (Aldrich) in 39.5 ml deionized $H_2O$. Tibial muscles of anaesthetized mice were shaved, and 20 µl of a solution containing 25 µg DNA were inoculated in each muscle. The DNA-containing solution was prepared just before use according to Dr. F. Pericle's instructions (Valentis, Inc., The Woodlands, Tex., USA). This solution contained plasmid DNA at a concentration of 1.25 mg/ml, poly-L-glutamate sodium salt (Sigma-Aldrich, S.r.l., Milan, Italy) at a concentration of 6 mg/ml, sodium chloride at a concentration of 150 mM (Fluka, BioChemika, Buchs, Switzerland), and endotoxin-free distillated water (Nucleare Free Water, Promega Corporation) to a final volume of 1 ml. After about 5 minutes of inoculation, two electrical pulses, 375 V/cm$^2$ in intensity and 25 msec in duration each, generated by an Electro Square Porator electroporator (T820, BTX, San Diego, Calif., USA) were applied to both tibial muscles of mice using two steel electrodes located 3 mm apart in a quadrangular arrangement laterally in the leg. Gene immunization by electroporation was performed twice in each animal 21 and 7 days before inoculating tumor cells.

Inoculation of Tumor Cells

Left sides of mice were inoculated with 0.2 ml of a suspension containing $2 \times 10^5$ TUBO cells.

In Vivo Tumor Growth Evaluation

Tumor growth was evaluated by palpation weekly, and tumor size was measured along two perpendicular diameters with a gauge. Neoplastic masses of a size larger than 1 millimeter were considered as tumors. Tumor growth was monitored for 100 days from tumor inoculation or until tumor size exceeded 10 millimeters in diameter, time at which animals were sacrificed. The results obtained demonstrate that chimeric pCMV3.1-HuRT5 plasmid is able to protect 100% of vaccinated BALB/c mice from a lethal inoculation of TUBO cells (Table 2).

TABLE 2

| Plasmids | N° mice | Protection | Survival (days) |
| --- | --- | --- | --- |
| pCMV3.1-neuL | 5 | 0% | +35 |
| pCMV3.1-neuL-rEC-TM | 5 | 100% | +100 |
| pCMV3.1-HuRT5 | 5 | 100% | +100 |

Evaluation of Anti-p185$^{neu}$ Antibody Presence in Sera of Vaccinated Animals

The day preceding the inoculation of tumor cells, blood was drawn from animals vaccinated with chimeric pCMV3.1-HuRT5 plasmid. Sera were analyzed to assess the presence of rat anti-p185$^{neu}$ antibodies. Sera were incubated for 45 minutes at 4° C. with cells overexpressing rat p185$^{neu}$. After washing with a solution called the washing buffer, which consists of phosphate buffer saline (PBS) containing 0.2% bovine serum albumin (BSA, Sigma, Milan, Italy) and 0.1% sodium azide (NaN$_3$, Sigma, Milan, Italy), samples were incubated for 20 minutes at 4° C. with an anti-mouse immunoglobulin FITC-conjugated antibody, washed with washing buffer, and analyzed by a FACScan cytofluorimeter (Becton Dickinson Immuno cytometry Systems, Mountain View, Calif., USA). Simultaneously, the same cells were incubated with decreasing concentrations of monoclonal anti-c-ErbB2/c-neu antibody (Ab4, Oncogene), so that a relationship between the fluorescence intensities obtained through cytofluorimeter analysis and concentration of anti-p185$^{neu}$ antibodies in animal sera could be derived. The data obtained show that all vaccinated animals exhibit high levels of anti-rat p185$^{neu}$ antibodies, and therefore chimeric pCMV3.1-HuRT5 plasmid is effective in inducing rejection of transplantable p185$^{neu}$-positive tumors and in eliciting a specific antibody response.

SEQUENCE LISTING

<160> NUMBER OF SEQ ID NOS: 35

<210> SEQ ID NO 1
<211> LENGTH: 1951
<212> TYPE: DNA
<213> ORGANISM: Rattus norvegicus

<400> SEQUENCE: 1

```
ccgggccgga gccgcaatga tcatcatgga gctggcggcc tggtgccgct ggggggttcct      60
cctcgccctc ctgccccccg gaatcgcgga attcctctca ttcctgcagg acatccagga     120
agttcagggt tacatgctca tcgctcacaa ccaggtgaag cgcgtcccac tgcaaaggct     180
gcgcatcgtg agagggaccc agctctttga ggacaagtat gccctggctg tgctagacaa     240
ccgagatcct caggacaatg tcgccgcctc caccccaggc agaacccccag aggggctgcg     300
ggagctgcag cttcgaagtc tcacagagat cctgaaggga ggagttttga tccgtgggaa     360
ccctcagctc tgctaccagg acatggtttt gtggaaggac gtcttccgca agaataacca     420
actggctcct gtcgatatag acaccaatcg ttcccgggcc tgtccaccctt gtgccccgc     480
ctgcaaagac aatcactgtt ggggtgagag tccggaagac tgtcagatct tgactggcac     540
catctgtacc agtggttgtg cccggtgcaa gggccggctg cccactgact gctgccatga     600
gcagtgtgcc gcaggctgca cgggccccaa gcattctgac tgcctggcct gcctccactt     660
caatcatagt ggtatctgtg agctgcactg cccagccctc gtcacctaca acacagacac     720
cttttgagtcc atgcacaacc ctgagggtcg ctacacctttt ggtgccagct gcgtgaccac     780
ctgcccctac aactacctgt ctacggaagt gggatcctgc actctggtgt gtccccccgaa     840
taaccaagag gtcacagctg aggacggaac acagcgttgt gagaaatgca gcaagccctg     900
tgctcgagtg tgctatggtc tgggcatgga gcaccttcga ggggcgaggg ccatcaccag     960
tgacaatgtc caggagtttg atggctgcaa gaagatcttt gggagcctgg catttttgcc    1020
ggagagcttt gatggggacc cctcctccgg cattgctccg ctgaggcctg agcagctcca    1080
agtgttcgaa accctggagg agatcacagg ttacctgtac atctcagcat ggccagacag    1140
tctccgtgac ctcagtgtct tccagaacct tcgaatcatt cggggacgga ttctccacga    1200
tggcgcgtac tcattgacac tgcaaggcct ggggatccac tcgctgggc tgcgctcact    1260
gcgggagctg gcagtggat tggctctgat tcaccgcaac gcccatctct gctttgtaca    1320
cactgtacct tgggaccagc tcttccggaa cccacatcag gccctgctcc acagtgggaa    1380
ccggccggaa gaggattgtg gtctcgaggg cttggtctgt aactcactgt gtgcccacgg    1440
gcactgctgg gggccagggc ccacccagtg tgtcaactgc agtcatttcc ttcggggcca    1500
ggagtgtgtg gaggagtgcc gagtatggaa ggggctcccc cgggagtatg tgagtgacaa    1560
gcgctgtctg ccgtgtcacc ccgagtgtca gcctcaaaac agctcagaga cctgcttttgg    1620
atcggaggct gatcagtgtg cagcctgcgc ccactacaag gactcgtcct cctgtgtggc    1680
tcgctgcccc agtggtgtga accggacct ctcctacatg cccatctgga gtacccgga    1740
tgaggagggc atatgccagc cgtgccccat caactgcacc cactcctgtg tggatctgga    1800
tgaacgaggc tgcccagcag agcagagagc cagcccggtg acattcatca ttgcaactgt    1860
agagggcgtc ctgctgttcc tgatcttagt ggtggtcgtt ggaatcctaa tcaaacgaag    1920
gagacagaag atccggaagt atacgatgta a                                    1951
```

<210> SEQ ID NO 2
<211> LENGTH: 1711
<212> TYPE: DNA
<213> ORGANISM: Rattus norvegicus

<400> SEQUENCE: 2

```
ccgggccgga gccgcaatga tcatcatgga gctggcggcc tggtgccgct ggggggttcct      60
cctcgccctc ctgccccccg gaatcgcgga attcaaggga ggagttttga tccgtgggaa     120
```

```
ccctcagctc tgctaccagg acatggtttt gtggaaggac gtcttccgca agaataacca    180
actggctcct gtcgatatag acaccaatcg ttcccgggcc tgtccacctt gtgccccgc     240 ctgcaaagac aatcactgtt ggggtgagag tccggaagac tgtcagatct tgactggcac    300
catctgtacc agtggttgtg cccggtgcaa gggccggctg cccactgact gctgccatga    360
gcagtgtgcc gcaggctgca cgggcccaa gcattctgac tgcctggcct gcctccactt     420
caatcatagt ggtatctgtg agctgcactg cccagccctc gtcacctaca acacagacac    480
ctttgagtcc atgcacaacc ctgagggtcg ctacaccttt ggtgccagct gcgtgaccac    540
ctgcccctac aactacctgt ctacggaagt gggatcctgc actctggtgt gtccccgaa     600 taaccaagag gtcacagctg aggacggaac acagcgttgt gagaaatgca gcaagccctg    660
tgctcgagtg tgctatggtc tgggcatgga gcaccttcga ggggcgaggg ccatcaccag    720
tgacaatgtc caggagtttg atggctgcaa gaagatcttt gggagcctgg cattttttgcc   780 ggagagcttt gatggggacc cctcctccgg cattgctccg ctgaggcctg agcagctcca    840
agtgttcgaa accctggagg agatcacagg ttacctgtac atctcagcat ggccagacag    900
tctccgtgac ctcagtgtct tccagaacct tcgaatcatt ggggacgga ttctccacga    960 tggcgcgtac tcattgacac tgcaaggcct ggggatccac tcgctggggc tgcgctcact   1020
gcgggagctg ggcagtggat tggctctgat tcaccgcaac gcccatctct gctttgtaca   1080
cactgtacct tgggaccagc tcttccggaa cccacatcag gccctgctcc acagtgggaa   1140
ccggccggaa gaggattgtg gtctcgaggg cttggtctgt aactcactgt gtgcccacgg   1200
gcactgctgg gggccagggc ccacccagtg tgtcaactgc agtcatttcc ttcggggcca   1260
ggagtgtgtg gaggagtgcc gagtatgaa ggggctcccc cgggagtatg tgagtgacaa    1320
gcgctgtctg ccgtgtcacc ccgagtgtca gcctcaaaac agctcagaga cctgctttgg   1380
atcggaggct gatcagtgtg cagcctgcgc ccactacaag gactcgtcct cctgtgtggc   1440
tcgctgcccc agtggtgtga accggaccct ctcctacatg cccatctgga agtacccgga   1500
tgaggagggc atatgccagc cgtgcccat caactgcacc cactcctgtg tggatctgga   1560
tgaacgaggc tgcccagcag agcagagagc cagcccggtg acattcatca ttgcaactgt   1620
agagggcgtc ctgctgttcc tgatcttagt ggtggtcgtt ggaatcctaa tcaaacgaag   1680
gagacagaag atccggaagt atacgatgta a                                  1711

<210> SEQ ID NO 3
<211> LENGTH: 1471
<212> TYPE: DNA
<213> ORGANISM: Rattus norvegicus

<400> SEQUENCE: 3
ccgggccgga gccgcaatga tcatcatgga gctggcggcc tggtgccgct gggggttcct    60
cctcgccctc ctgccccccg gaatcgcgga attccggctg cccactgact gctgccatga   120
gcagtgtgcc gcaggctgca cgggcccaa gcattctgac tgcctggcct gcctccactt    180
caatcatagt ggtatctgtg agctgcactg cccagccctc gtcacctaca acacagacac    240
ctttgagtcc atgcacaacc ctgagggtcg ctacaccttt ggtgccagct gcgtgaccac    300
ctgcccctac aactacctgt ctacggaagt gggatcctgc actctggtgt gtccccgaa     360 taaccaagag gtcacagctg aggacggaac acagcgttgt gagaaatgca gcaagccctg    420
tgctcgagtg tgctatggtc tgggcatgga gcaccttcga ggggcgaggg ccatcaccag    480
tgacaatgtc caggagtttg atggctgcaa gaagatcttt gggagcctgg cattttttgcc   540
```

```
ggagagcttt gatggggacc cctcctccgg cattgctccg ctgaggcctg agcagctcca    600
agtgttcgaa accctggagg agatcacagg ttacctgtac atctcagcat ggccagacag    660
tctccgtgac ctcagtgtct tccagaacct tcgaatcatt cggggacgga ttctccacga    720
tggcgcgtac tcattgacac tgcaaggcct ggggatccac tcgctggggc tgcgctcact    780
gcgggagctg ggcagtggat tggctctgat tcaccgcaac gcccatctct gctttgtaca    840
cactgtacct tgggaccagc tcttccggaa cccacatcag gccctgctcc acagtgggaa    900
ccggccggaa gaggattgtg gtctcgaggg cttggtctgt aactcactgt gtgcccacgg    960
gcactgctgg gggccagggc ccacccagtg tgtcaactgc agtcatttcc ttcggggcca    1020
ggagtgtgtg gaggagtgcc gagtatgaa gggctcccc cgggagtatg tgagtgacaa     1080
gcgctgtctg ccgtgtcacc ccgagtgtca gcctcaaaac agctcagaga cctgctttgg    1140
atcggaggct gatcagtgtg cagcctgcgc ccactacaag gactcgtcct cctgtgtggc    1200
tcgctgcccc agtggtgtga accggacct ctcctacatg cccatctgga agtacccgga    1260
tgaggagggc atatgccagc cgtgccccat caactgcacc cactcctgtg tggatctgga    1320
tgaacgaggc tgcccagcag agcagagagc cagcccggtg acattcatca ttgcaactgt    1380
agagggcgtc ctgctgttcc tgatcttagt ggtggtcgtt ggaatcctaa tcaaacgaag    1440
gagacagaag atccggaagt atacgatgta a                                   1471

<210> SEQ ID NO 4
<211> LENGTH: 1231
<212> TYPE: DNA
<213> ORGANISM: Rattus norvegicus

<400> SEQUENCE: 4
ccgggccgga gccgcaatga tcatcatgga gctggcggcc tggtgccgct gggggttcct     60
cctcgccctc ctgcccccg gaatcgcgga attctcctgc actctggtgt gtccccgaa     120 taaccaagag gtcacagctg aggacggaac acagcgttgt gagaaatgca gcaagccctg    180
tgctcgagtg tgctatggtc tgggcatgga gcaccttcga ggggcgaggg ccatcaccag    240
tgacaatgtc caggagtttg atggctgcaa gaagatcttt gggagcctgg cattttttgcc    300 ggagagcttt gatggggacc cctcctccgg cattgctccg ctgaggcctg agcagctcca    360
agtgttcgaa accctggagg agatcacagg ttacctgtac atctcagcat ggccagacag    420
tctccgtgac ctcagtgtct tccagaacct tcgaatcatt cggggacgga ttctccacga    480
tggcgcgtac tcattgacac tgcaaggcct ggggatccac tcgctggggc tgcgctcact    540
gcgggagctg ggcagtggat tggctctgat tcaccgcaac gcccatctct gctttgtaca    600
cactgtacct tgggaccagc tcttccggaa cccacatcag gccctgctcc acagtgggaa    660
ccggccggaa gaggattgtg gtctcgaggg cttggtctgt aactcactgt gtgcccacgg    720
gcactgctgg gggccagggc ccacccagtg tgtcaactgc agtcatttcc ttcggggcca    780
ggagtgtgtg gaggagtgcc gagtatgaa gggctcccc cgggagtatg tgagtgacaa     840
gcgctgtctg ccgtgtcacc ccgagtgtca gcctcaaaac agctcagaga cctgctttgg    900
atcggaggct gatcagtgtg cagcctgcgc ccactacaag gactcgtcct cctgtgtggc    960
tcgctgcccc agtggtgtga accggacct ctcctacatg cccatctgga agtacccgga    1020
tgaggagggc atatgccagc cgtgccccat caactgcacc cactcctgtg tggatctgga    1080
tgaacgaggc tgcccagcag agcagagagc cagcccggtg acattcatca ttgcaactgt    1140
agagggcgtc ctgctgttcc tgatcttagt ggtggtcgtt ggaatcctaa tcaaacgaag    1200
```
gagacagaag atccggaagt atacgatgta a                                      1231

<210> SEQ ID NO 5
<211> LENGTH: 991
<212> TYPE: DNA
<213> ORGANISM: Rattus norvegicus

<400> SEQUENCE: 5

| | |
|---|---|
| ccgggccgga gccgcaatga tcatcatgga gctggcggcc tggtgccgct ggggggttcct | 60 |
| cctcgccctc ctgcccccg gaatcgcgga attcgctccg ctgaggcctg agcagctcca | 120 |
| agtgttcgaa accctggagg agatcacagg ttacctgtac atctcagcat ggccagacag | 180 |
| tctccgtgac ctcagtgtct tccagaacct tcgaatcatt cggggacgga ttctccacga | 240 |
| tggcgcgtac tcattgacac tgcaaggcct ggggatccac tcgctggggc tgcgctcact | 300 |
| gcgggagctg ggcagtggat tggctctgat tcaccgcaac gcccatctct gctttgtaca | 360 |
| cactgtacct tgggaccagc tcttccgaaa cccacatcag gccctgctcc acagtgggaa | 420 |
| ccggccggaa gaggattgtg gtctcgaggg cttggtctgt aactcactgt gtgcccacgg | 480 |
| gcactgctgg gggccagggc ccacccagtg tgtcaactgc agtcatttcc ttcgggggcca | 540 |
| ggagtgtgtg gaggagtgcc gagtatggaa ggggctcccc cgggagtatg tgagtgacaa | 600 |
| gcgctgtctg ccgtgtcacc ccgagtgtca gcctcaaaac agctcagaga cctgctttgg | 660 |
| atcggaggct gatcagtgtg cagcctgcgc ccactacaag gactcgtcct cctgtgtggc | 720 |
| tcgctgcccc agtggtgtga accggacct ctcctacatg cccatctgga gtacccgga | 780 |
| tgaggagggc atatgccagc cgtgccccat caactgcacc cactcctgtg tggatctgga | 840 |
| tgaacgaggc tgcccagcag agcagagagc cagcccggtg acattcatca ttgcaactgt | 900 |
| agagggcgtc ctgctgttcc tgatcttagt ggtggtcgtt ggaatcctaa tcaaacgaag | 960 |
| gagacagaag atccggaagt atacgatgta a | 991 |

<210> SEQ ID NO 6
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 6

| | |
|---|---|
| cggagccgca gtgagcacca tggagctggc ggccttgtgc cgctgggggc tcctcctcgc | 60 |
| cctcttgccc cccggagccg cgagcaccca agtgtgcacc ggcacagaca tgaagctgcg | 120 |
| gctccctgcc agtcccgaga cccacctgga catgctccgc cacctctacc agggctgcca | 180 |
| ggtggtgcag ggaaacctgg aactcaccta cctgcccacc aatgccagcg aattcctctc | 240 |
| attcctgcag gacatccagg aagttcaggg ttacatgctc atcgctcaca accaggtgaa | 300 |
| gcgcgtccca ctgcaaaggc tgcgcatcgt gagagggacc cagctctttg aggacaagta | 360 |
| tgcccctggct gtgctagaca accgagatcc tcaggacaat gtcgccgcct ccacccagg | 420 |
| cagaacccca gaggggctgc gggagctgca gcttcgaagt ctcacagaga tcctgaaggg | 480 |
| aggagttttg atccgtggga accctcagct ctgctaccag acatggtttt gtgaagga | 540 |
| cgtcttccgc aagaataacc aactggctcc tgtcgatata gacaccaatc gttcccgggc | 600 |
| ctgtccacct tgtgcccccg cctgcaaaga caatcactgt tggggtgaga gtccggaaga | 660 |
| ctgtcagatc ttgactggca ccatctgtac cagtggttgt gccggtgca agggccggct | 720 |
| gcccactgac tgctgtcatg agcagtgtgc cgcaggctgc acgggcccca gcattctga | 780 |

```
ctgcctggcc tgcctccact tcaatcatag tggtatctgt gagctgcact gcccagccct    840
cgtcacctac aacacagaca cctttgagtc catgcacaac cctgagggtc gctacacctt    900
tggtgccagc tgcgtgacca cctgccccta caactacctg tctacggaag tgggatcctg    960
cactctggtg tgtcccccga ataaccaaga ggtcacagct gaggacggaa cacagcgttg   1020
tgagaaatgc agcaagccct gtgctcgagt gtgctatggt ctgggcatgg agcaccttcg   1080
aggggcgagg gccatcacca gtgacaatgt ccaggagttt gatggctgca agaagatctt   1140
tgggagcctg gcattttttgc cggagagctt tgatggggac ccctcctccg gcattgctcc   1200
gctgaggcct gagcagctcc aagtgttcga accctggag gagatcacag gttacctgta    1260
catctcagca tggccagaca gtctccgtga cctcagtgtc ttccagaacc ttcgaatcat   1320
tcggggacgg attctccacg atggcgcgta ctcattgaca ctgcaaggcc tggggatcca   1380
ctcgctgggg ctgcgctcac tgcgggagct gggcagtgga ttggctctga ttcaccgcaa   1440
cgcccatctc tgctttgtac acactgtacc ttgggaccag ctcttccgga acccacatca   1500
ggccctgctc cacagtggga accggccgga agaggattgt ggtctcgagg gcttggtctg   1560
taactcactg tgtgccccacg ggcactgctg ggggccaggg cccacccagt gtgtcaactg   1620
cagtcatttc cttcggggcc aggagtgtgt ggaggagtgc cgagtatgga aggggctccc   1680
ccgggagtat gtgagtgaca agcgctgtct gccgtgtcac cccgagtgtc agcctcaaaa   1740
cagctcagag acctgctttg gatcggaggc tgatcagtgt gcagcctgcg cccactacaa   1800
ggactcgtcc tcctgtgtgg ctcgctgccc cagtggtgtg aaaccggacc tctcctacat   1860
gcccatctgg aagtacccgg atgaggaggg catatgccag ccgtgcccca tcaactgcac   1920
ccactcctgt gtggatctgg atgaacgagg ctgcccagca gagcagagag ccagcccggt   1980
gacattcatc attgcaactg tagagggcgt cctgctgttc ctgatcttag tggtggtcgt   2040
tggaatccta atcaaacgaa ggagacagaa gatccggaag tatacgatgt aa            2092

<210> SEQ ID NO 7
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 7
cggagccgca gtgagcacca tggagctggc ggccttgtgc cgctgggggc tcctcctcgc     60
cctcttgccc cccggagccg cgagcaccca agtgtgcacc ggcacagaca tgaagctgcg    120
gctccctgcc agtcccgaga cccacctgga catgctccgc cacctctacc agggctgcca    180
ggtggtgcag ggaaacctgg aactcaccta cctgcccacc aatgccagcc tgtccttcct    240
gcaggatatc caggaggtgc agggctacgt gctcatcgct cacaaccaag tgaggcaggt    300
cccactgcag aggctgcgga ttgtgcgagg cacccagctc tttgaggaca ctatgccct    360 ggccgtgcta gacaatggag acccgctgaa caataccacc cctgtcacag ggcctcccc    420 aggaggcctg cgggagctgc agcttcgaag cctcacagag atcttgaaag aattcaaggg    480
aggagttttg atccgtggga accctcagct ctgctaccag gacatggttt tgtggaagga    540
cgtcttccgc aagaataacc aactggcctc cgtcgatata gacaccaatc gttcccgggc    600
ctgtccacct tgtgcccccg cctgcaaaga caatcactgt tggggtgaga gtccggaaga    660
ctgtcagatc ttgactggca ccatctgtac cagtggttgt gcccggtgca gggccggct    720 gcccactgac tgctgccatg agcagtgtgc cgcaggctgc acgggcccca gcattctga    780
```

```
ctgcctggcc tgcctccact tcaatcatag tggtatctgt gagctgcact gcccagccct    840
cgtcacctac aacacagaca cctttgagtc catgcacaac cctgagggtc gctacacctt    900
tggtgccagc tgcgtgacca cctgccccta caactacctg tctacggaag tgggatcctg    960
cactctggtg tgtccccga ataaccaaga ggtcacagct gaggacggaa cacagcgttg   1020
tgagaaatgc agcaagccct gtgctcgagt gtgctatggt ctgggcatgg agcaccttcg   1080
aggggcgagg gccatcacca gtgacaatgt ccaggagttt gatggctgca agaagatctt   1140
tgggagcctg gcatttttgc cggagagctt tgatggggac ccctcctccg gcattgctcc   1200
gctgaggcct gagcagctcc aagtgttcga accctggag gagatcacag gttacctgta   1260
catctcagca tggccagaca gtctccgtga cctcagtgtc ttccagaacc ttcgaatcat   1320
tcggggacgg attctccacg atggcgcgta ctcattgaca ctgcaaggcc tggggatcca   1380
ctcgctgggg ctgcgctcac tgcgggagct gggcagtgga ttggctctga ttcaccgcaa   1440
cgcccatctc tgctttgtac acactgtacc ttgggaccag ctcttccgga acccacatca   1500
ggccctgctc cacagtggga accggccgga agaggattgt ggtctcgagg gcttggtctg   1560
taactcactg tgtgccccacg ggcactgctg ggggccaggg cccacccagt gtgtcaactg   1620
cagtcatttc cttcggggcc aggagtgtgt ggaggagtgc cgagtatgga agggctccc   1680 ccgggagtat gtgagtgaca agcgctgtct gccgtgtcac cccgagtgtc agcctcaaaa   1740
cagctcagag acctgctttg gatcggaggc tgatcagtgt gcagcctgcg cccactacaa   1800
ggactcgtcc tcctgtgtgg ctcgctgccc cagtggtgtg aaaccggacc tctcctacat   1860
gcccatctgg aagtacccgg atgaggaggg catatgccag ccgtgcccca tcaactgcac   1920
ccactcctgt gtggatctgg atgaacgagg ctgcccagca gagcagagag ccagcccggt   1980
gacattcatc attgcaactg tagagggcgt cctgctgttc ctgatcttag tggtggtcgt   2040
tggaatccta atcaaacgaa ggagacagaa gatccggaag tatacgatgt aa             2092

<210> SEQ ID NO 8
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 8
cggagccgca gtgagcacca tggagctggc ggccttgtgc cgctgggggc tcctcctcgc     60
cctcttgccc cccggagccg cgagcaccca agtgtgcacc ggcacagaca tgaagctgcg    120
gctccctgcc agtcccgaga cccacctgga catgctccgc cacctctacc agggctgcca    180
ggtggtgcag ggaaacctgg aactcaccta cctgcccacc aatgccagcc tgtccttcct    240
gcaggatatc caggaggtgc agggctacgt gctcatcgct cacaaccaag tgaggcaggt    300
cccactgcag aggctgcgga ttgtgcgagg cacccagctc tttgaggaca ctatgccct     360 ggccgtgcta gacaatggag acccgctgaa caataccacc cctgtcacag ggcctccc     420 aggaggcctg cgggagctgc agcttcgaag cctcacagag atcttgaaag agggtctct     480 gatccagcgg aaccccagc tctgctacca ggacacgatt ttgtggaagg acatcttcca    540
caagaacaac cagctggctc tcacactgat agacaccaac cgctctcggg cctgccaccc    600
ctgttctccg atgtgtaagg gctcccgctg ctggggagag agttctgagg attgtcagag    660
cctgacgcgc actgtctgtg ccggtggctg tgcccgctgc aaggggccag aattccggct    720
gccccactga ctgctgccatg agcagtgtgc cgcaggctgc acgggcccca gcattctga    780
```

```
ctgcctggcc tgcctccact tcaatcatag tggtatctgt gagctgcact gcccagccct    840
cgtcacctac aacacagaca cctttgagtc catgcacaac cctgagggtc gctacacctt    900
tggtgccagc tgcgtgacca cctgccccta caactacctg tctacggaag tgggatcctg    960
cactctggtg tgtccccga ataaccaaga ggtcacagct gaggacggaa cacagcgttg    1020
```
(Note: original reads "tgtccccga" per image)

```
tgagaaatgc agcaagccct gtgctcgagt gtgctatggt ctgggcatgg agcaccttcg    1080
aggggcgagg gccatcacca gtgacaatgt ccaggagttt gatggctgca agaagatctt    1140
tgggagcctg gcattttgc cggagagctt tgatggggac ccctcctccg gcattgctcc    1200
gctgaggcct gagcagctcc aagtgttcga accctggag gagatcacag gttacctgta    1260
catctcagca tggccagaca gtctccgtga cctcagtgtc ttccagaacc ttcgaatcat    1320
tcggggacgg attctccacg atggcgcgta ctcattgaca ctgcaaggcc tggggatcca    1380
ctcgctgggg ctgcgctcac tgcgggagct gggcagtgga ttggctctga ttcaccgcaa    1440
cgcccatctc tgctttgtac acactgtacc ttgggaccag ctcttccgga acccacatca    1500
ggccctgctc cacagtggga accggccgga agaggattgt ggtctcgagg gcttggtctg    1560
taactcactg tgtgcccacg ggcactgctg ggggccaggg cccacccagt gtgtcaactg    1620
cagtcatttc cttcggggcc aggagtgtgt ggaggagtgc cgagtatgga aggggctccc    1680 ccggagtat gtgagtgaca agcgctgtct gccgtgtcac cccgagtgtc agcctcaaaa    1740
```
(Note: original reads "ccggagtat" per image)

```
cagctcagag acctgctttg gatcggaggc tgatcagtgt gcagcctgcg cccactacaa    1800
ggactcgtcc tcctgtgtgg ctcgctgccc cagtggtgtg aaaccggacc tctcctacat    1860
gcccatctgg aagtacccgg atgaggaggg catatgccag ccgtgcccca tcaactgcac    1920
ccactcctgt gtggatctgg atgaacgagg ctgcccagca gagcagagag ccagcccggt    1980
gacattcatc attgcaactg tagagggcgt cctgctgttc ctgatcttag tggtggtcgt    2040
tggaatccta atcaaacgaa ggagacagaa gatccggaag tatacgatgt aa    2092

<210> SEQ ID NO 9
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 9
cggagccgca gtgagcacca tggagctggc ggccttgtgc cgctgggggc tcctcctcgc    60
cctcttgccc cccggagccg cgagcaccca agtgtgcacc ggcacagaca tgaagctgcg    120
gctccctgcc agtcccgaga cccacctgga catgctccgc cacctctacc agggctgcca    180
ggtggtgcag ggaaacctgg aactcaccta cctgcccacc aatgccagcc tgtccttcct    240
gcaggatatc caggaggtgc agggctacgt gctcatcgct cacaaccaag tgaggcaggt    300
cccactgcag aggctgcgga ttgtgcgagg cacccagctc tttgaggaca actatgccct    360
ggccgtgcta gacaatggag acccgctgaa caataccacc cctgtcacag ggcctcccc    420
```
(Note: original reads "ggcctcccc" per image)

```
aggaggcctg cgggagctgc agcttcgaag cctcacagag atcttgaaag gaggggtctt    480
gatccagcgg aacccccagc tctgctacca ggacacgatt ttgtggaagg acatcttcca    540
caagaacaac cagctggctc tcacactgat agacaccaac cgctctcggg cctgccaccc    600
ctgttctccg atgtgtaagg gctcccgctg ctggggagag agttctgagg attgtcagag    660
cctgacgcgc actgtctgtg ccggtggctg tgccgctgc aaggggccac tgcccactga    720
```
(Note: original reads "tgccgctgc" per image)

```
ctgctgccat gagcagtgtg ctgccggctg cacgggcccc aagcactctg actgcctggc    780
```

```
ctgcctccac ttcaaccaca gtggcatctg tgagctgcac tgcccagccc tggtcaccta      840
caacacagac acgtttgagt ccatgcccaa tcccgagggc cggtatacat tcggcgccag      900
ctgtgtgact gcctgtccct acaactacct ttctacggac gtgggatccg aattctcctg      960
cactctggtg tgtccccga ataaccaaga ggtcacagct gaggacggaa cacagcgttg     1020
tgagaaatgc agcaagccct gtgctcgagt gtgctatggt ctgggcatgg agcaccttcg     1080
aggggcgagg gccatcacca gtgacaatgt ccaggagttt gatggctgca agaagatctt     1140
tgggagcctg gcattttttgc cggagagctt tgatggggac ccctcctccg gcattgctcc     1200
gctgaggcct gagcagctcc aagtgttcga accctggag gagatcacag gttacctgta      1260
catctcagca tggccagaca gtctccgtga cctcagtgtc ttccagaacc ttcgaatcat     1320
tcggggacgg attctccacg atggcgcgta ctcattgaca ctgcaaggcc tggggatcca     1380
ctcgctgggg ctgcgctcac tgcgggagct gggcagtgga ttggctctga ttcaccgcaa     1440
cgcccatctc tgctttgtac acactgtacc ttgggaccag ctcttccgga acccacatca     1500
ggccctgctc cacagtggga accggccgga agaggattgt ggtctcgagg gcttggtctg     1560
taactcactg tgtgcccacg ggcactgctg ggggccaggg cccacccagt gtgtcaactg     1620
cagtcatttc cttcggggcc aggagtgtgt ggaggagtgc cgagtatgga aggggctccc     1680
ccgggagtat gtgagtgaca gcgctgtct gccgtgtcac cccgagtgtc agcctcaaaa     1740
cagctcagag acctgctttg gatcggaggc tgatcagtgt gcagcctgcg cccactacaa     1800
ggactcgtcc tcctgtgtgg ctcgctgccc cagtggtgtg aaaccggacc tctcctacat     1860
gcccatctgg aagtacccgg atgaggaggg catatgccag ccgtgcccca tcaactgcac     1920
ccactcctgt gtggatctgg atgaacgagg ctgcccagca gagcagagag ccagcccggt     1980
gacattcatc attgcaactg tagagggcgt cctgctgttc ctgatcttag tggtggtcgt     2040
tggaatccta atcaaacgaa ggagacagaa gatccggaag tatacgatgt aa              2092

<210> SEQ ID NO 10
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 10
cggagccgca gtgagcacca tggagctggg ggccttgtgc cgctgggggc tcctcctcgc       60
cctcttgccc cccggagccg cgagcaccca agtgtgcacc ggcacagaca tgaagctgcg      120
gctccctgcc agtcccgaga cccacctgga catgctccgc cacctctacc agggctgcca      180
ggtggtgcag ggaaacctgg aactcaccta cctgcccacc aatgccagcc tgtccttcct      240
gcaggatatc caggaggtgc agggctacgt gctcatcgct cacaaccaag tgaggcaggt      300
cccactgcag aggctgcgga ttgtgcgagg cacccagctc tttgaggaca actatgccct      360
ggccgtgcta gacaatggag acccgctgaa caataccacc cctgtcacag ggcctcccc      420 aggaggcctg cgggagctgc agcttcgaag cctcacagag atcttgaaag aggggtctct      480
gatccagcgg aaccccagc tctgctacca ggacacgatt ttgtggaagg acatcttcca      540
caagaacaac cagctggctc tcacactgat agacaccaac cgctctcggg cctgccaccc      600
ctgttctccg atgtgtaagg ctcccgctg ctggggagag agttctgagg attgtcagag      660
cctgacgcgc actgtctgtg ccggtggctg tgcccgctgc aaggggccac tgcccactga      720
ctgctgccat gagcagtgtg ctgccggctg cacgggcccc aagcactctg actgcctggc      780
```

```
ctgcctccac ttcaaccaca gtggcatctg tgagctgcac tgcccagccc tggtcaccta    840
caacacagac acgtttgagt ccatgcccaa tcccgagggc cggtatacat tcggcgccag    900
ctgtgtgact gcctgtccct acaactacct ttctacggac gtgggatcct gcaccctcgt    960
ctgccccctg cacaaccaag aggtgacagc agaggatgga acacagcggt gtgagaagtg   1020
cagcaagccc tgtgcccgag tgtgctatgg tctgggcatg gagcacttgc gagaggtgag   1080
ggcagttacc agtgccaata tccaggagtt tgctggctgc aagaagatct ttgggagcct   1140
ggcatttctg ccggagagct ttgatgggga cccagcctcc aacactgccg aattcgctcc   1200
gctgaggcct gagcagctcc aagtgttcga aaccctggag gagatcacag gttacctgta   1260
catctcagca tggccagaca gtctccgtga cctcagtgtc ttccagaacc ttcgaatcat   1320
tcggggacgg attctccacg atggcgcgta ctcattgaca ctgcaaggcc tggggatcca   1380
ctcgctgggg ctgcgctcac tgcgggagct gggcagtgga ttggctctga ttcaccgcaa   1440
cgcccatctc tgctttgtac acactgtacc ttgggaccag ctcttccgga acccacatca   1500
ggccctgctc cacagtggga accggccgga agaggattgt ggtctcgagg gcttggtctg   1560
taactcactg tgtgcccacg ggcactgctg ggggccaggg cccacccagt gtgtcaactg   1620
cagtcatttc cttcggggcc aggagtgtgt ggaggagtgc cgagtatgga aggggctccc   1680
ccgggagtat gtgagtgaca agcgctgtct gccgtgtcac cccgagtgtc agcctcaaaa   1740
cagctcagag acctgctttg gatcggaggc tgatcagtgt gcagcctgcg cccactacaa   1800
ggactcgtcc tcctgtgtgg ctcgctgccc cagtggtgtg aaaccggacc tctcctacat   1860
gcccatctgg aagtacccgg atgaggaggg catatgccag ccgtgcccca tcaactgcac   1920
ccactcctgt gtggatctgg atgaacgagg ctgcccagca gagcagagag ccagcccggt   1980
gacattcatc attgcaactg tagagggcgt cctgctgttc ctgatcttag tggtggtcgt   2040
tggaatccta atcaaacgaa ggagacagaa gatccggaag tatacgatgt aa            2092

<210> SEQ ID NO 11
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 11
cggagccgca gtgagcacca tggagctggg ggccttgtgc cgctgggggc tcctcctcgc     60
cctcttgccc cccggagccg cgagcaccca agtgtgcacc ggcacagaca tgaagctgcg    120
gctccctgcc agtcccgaga cccacctgga catgctccgc cacctctacc agggctgcca    180
ggtggtgcag ggaaacctgg aactcaccta cctgcccacc aatgccagcc tgtccttcct    240
gcaggatatc caggaggtgc agggctacgt gctcatcgct cacaaccaag tgaggcaggt    300
cccactgcag aggctgcgga ttgtgcgagg cacccagctc tttgaggaca ctatgccct    360 ggccgtgcta gacaatggag acccgctgaa caataccacc cctgtcacag ggcctccc    420 aggaggcctc cgggagctgc agcttcgaag cctcacagag atcttgaaag gagggtctt    480 gatccagcgg aaccccagc tctgctacca ggacacgatt ttgtggaagg acatcttcca    540
caagaacaac cagctggctc tcacactgat agacaccaac cgctctcggg cctgccaccc    600
ctgttctccg atgtgtaagg gctcccgctg ctggggagag agttctgagg attgtcagag    660
cctgacgcgc actgtctgtg ccggtggctg tgccgctgc aaggggccac tgcccactga    720
ctgctgccat gagcagtgtg ctgccggctg cacgggcccc aagcactctg actgcctggc    780
```

```
ctgcctccac ttcaaccaca gtggcatctg tgagctgcac tgcccagccc tggtcaccta    840
caacacagac acgtttgagt ccatgcccaa tcccgagggc cggtatacat tcggcgccag    900
ctgtgtgact gcctgtccct acaactacct ttctacggac gtgggatcct gcaccctcgt    960 ctgcccctg cacaaccaag aggtgacagc agaggatgga acacagcggt gtgagaagtg    1020
cagcaagccc tgtgcccgag tgtgctatgg tctgggcatg gagcacttgc gagaggtgag    1080
ggcagttacc agtgccaata tccaggagtt tgctggctgc aagaagatct ttgggagcct    1140
ggcatttctg ccggagagct ttgatgggga cccagcctcc aacactgccc cgctccagcc    1200
agagcagctc caagtgtttg agactctgga agagatcaca ggttacctat acatctcagc    1260
atggccggac agcctgcctg acctcagcgt cttccagaac ctgcaagtaa tccggggacg    1320
aattctgcac aatggcgcct actcgctgac cctgcaaggg ctgggcatca gctggctggg    1380
gctgcgctca ctgagggaac tgggcagtgg actggccctc atccaccatg ctagccgcaa    1440
cgcccatctc tgctttgtac acactgtacc ttgggaccag ctcttccgga acccacatca    1500
ggccctgctc cacagtggga accggccgga agaggattgt ggtctcgagg cttggtctg    1560 taactcactg tgtgcccacg ggcactgctg ggggccaggg cccacccagt gtgtcaactg    1620
cagtcatttc cttcggggcc aggagtgtgt ggaggagtgc cgagtatgga aggggctccc    1680
ccgggagtat gtgagtgaca agcgctgtct gccgtgtcac cccgagtgtc agcctcaaaa    1740
cagctcagag acctgctttg gatcggaggc tgatcagtgt gcagcctgcg cccactacaa    1800
ggactcgtcc tcctgtgtgg ctcgctgccc cagtggtgtg aaaccggacc tctcctacat    1860
gcccatctgg aagtacccgg atgaggaggg catatgccag ccgtgcccca tcaactgcac    1920
ccactcctgt gtggatctgg atgaacgagg ctgcccagca gagcagagag ccagcccggt    1980
gacattcatc attgcaactg tagagggcgt cctgctgttc ctgatcttag tggtggtcgt    2040
tggaatccta atcaaacgaa ggagacagaa gatccggaag tatacgatgt aa            2092

<210> SEQ ID NO 12
<211> LENGTH: 2092
<212> TYPE: DNA
<213> ORGANISM: Unknown
<220> FEATURE:
<223> OTHER INFORMATION: homo sapiens/rattus norvegicus chimera

<400> SEQUENCE: 12
cggagccgca gtgagcacca tggagctggc ggccttgtgc cgctgggggc tcctcctcgc    60
cctcttgccc cccggagccg cgagcaccca agtgtgcacc ggcacagaca tgaagctgcg    120
gctccctgcc agtcccgaga cccacctgga catgctccgc cacctctacc agggctgcca    180
ggtggtgcag ggaaacctgg aactcaccta cctgcccacc aatgccagcc tgtccttcct    240
gcaggatatc caggaggtgc agggctacgt gctcatcgct cacaaccaag tgaggcaggt    300
cccactgcag aggctgcgga ttgtgcgagg cacccagctc tttgaggaca ctatgccct    360 ggccgtgcta gacaatggag acccgctgaa caataccacc cctgtcacag ggcctccc    420 aggaggcctg cggagctgc agcttcgaag cctcacagag atcttgaaag gaggggtctt    480
gatccagcgg aaccccagc tctgctacca ggacacgatt ttgtggaagg acatcttcca    540
caagaacaac cagctggctc tcacactgat agacaccaac cgctctcggg cctgccaccc    600
ctgttctccg atgtgtaagg gctcccgctg ctgggggag agttctgagg attgtcagag    660
cctgacgcgc actgtctgtg ccggtggctg tgcccgctgc aaggggccac tgcccactga    720
ctgctgccat gagcagtgtg ctgccggctg cacgggcccc aagcactctg actgcctggc    780
```

-continued

```
ctgcctccac ttcaaccaca gtggcatctg tgagctgcac tgcccagccc tggtcaccta    840
caacacagac acgtttgagt ccatgcccaa tcccgagggc cggtatacat tcggcgccag    900
ctgtgtgact gcctgtccct acaactacct ttctacggac gtgggatcct gcaccctcgt    960
ctgccccctg cacaaccaag aggtgacagc agaggatgga acacagcggt gtgagaagtg   1020
cagcaagccc tgtgcccgag tgtgctatgg tctgggcatg gagcacttgc gagaggtgag   1080
ggcagttacc agtgccaata tccaggagtt tgctggctgc aagaagatct ttgggagcct   1140
ggcatttctg ccggagagct ttgatgggga cccagcctcc aacactgccc cgctccagcc   1200
agagcagctc caagtgtttg agactctgga agagatcaca ggttacctat acatctcagc   1260
atggccggac agcctgcctg acctcagcgt cttccagaac ctgcaagtaa tccggggacg   1320
aattctgcac aatggcgcct actcgctgac cctgcaaggg ctgggcatca gctggctggg   1380
gctgcgctca ctgagggaac tgggcagtgg actggccctc atccaccata cacccacct   1440 ctgcttcgtg cacacggtgc cctgggacca gctctttcgg aacccgcacc aagctctgct   1500
ccacactgcc aaccggccag aggacgagtg tgtgggcgag ggcctggcct gccaccagct   1560
gtgcgcccga gggcactgct gggtccagg gcccacccag tgtgtcaact gcagccagtt   1620
ccttcggggc caggagtgcg tggaggaatg ccgagtactg caggggctcg ctagcctccc   1680
ccgggagtat gtgagtgaca agcgctgtct gccgtgtcac cccgagtgtc agcctcaaaa   1740
cagctcagag acctgctttg gatcggaggc tgatcagtgt gcagcctgcg cccactacaa   1800
ggactcgtcc tcctgtgtgg ctcgctgccc cagtggtgtg aaaccggacc tctcctacat   1860
gcccatctgg aagtacccgg atgaggaggg catatgccag ccgtgcccca tcaactgcac   1920
ccactcctgt gtggatctgg atgaacgagg ctgcccagca gagcagagag ccagcccggt   1980
gacattcatc attgcaactg tagagggcgt cctgctgttc ctgatcttag tggtggtcgt   2040
tggaatccta atcaaacgaa ggagacagaa gatccggaag tatacgatgt aa           2092
```

<210> SEQ ID NO 13
<211> LENGTH: 20
<212> TYPE: DNA
<213> ORGANISM: Unknown
<220> FEATURE:
<223> OTHER INFORMATION: synthetic oligonucleotide

<400> SEQUENCE: 13

```
taatacgact cactataggg                                                  20
```

<210> SEQ ID NO 14
<211> LENGTH: 30
<212> TYPE: DNA
<213> ORGANISM: Unknown
<220> FEATURE:
<223> OTHER INFORMATION: synthetic oligonucleotide

<400> SEQUENCE: 14

```
catggaattc cgcgattccg gggggcagga                                       30
```

<210> SEQ ID NO 15
<211> LENGTH: 30
<212> TYPE: DNA
<213> ORGANISM: Unknown
<220> FEATURE:
<223> OTHER INFORMATION: synthetic oligonucleotide

<400> SEQUENCE: 15

```
catggaattc ctctcattcc tgcaggacat                                       30
```

<210> SEQ ID NO 16
<211> LENGTH: 30
<212> TYPE: DNA
<213> ORGANISM: Unknown
<220> FEATURE:
<223> OTHER INFORMATION: synthetic oligonucleotide

<400> SEQUENCE: 16
catggaattc aagggaggag ttttgatccg                                    30

<210> SEQ ID NO 17
<211> LENGTH: 30
<212> TYPE: DNA
<213> ORGANISM: Unknown
<220> FEATURE:
<223> OTHER INFORMATION: synthetic oligonucleotide

<400> SEQUENCE: 17
catggaattc cggctgccca ctgactgctg                                    30

<210> SEQ ID NO 18
<211> LENGTH: 30
<212> TYPE: DNA
<213> ORGANISM: Unknown
<220> FEATURE:
<223> OTHER INFORMATION: synthetic oligonucleotide

<400> SEQUENCE: 18
catggaattc tcctgcactc tggtgtgtcc                                    30

<210> SEQ ID NO 19
<211> LENGTH: 30
<212> TYPE: DNA
<213> ORGANISM: Unknown
<220> FEATURE:
<223> OTHER INFORMATION: synthetic oligonucleotide

<400> SEQUENCE: 19
catggaattc gctccgctga ggcctgagca                                    30

<210> SEQ ID NO 20
<211> LENGTH: 30
<212> TYPE: DNA
<213> ORGANISM: Unknown
<220> FEATURE:
<223> OTHER INFORMATION: synthetic oligonucleotide

<400> SEQUENCE: 20
catggaattc cgcaacgccc atctctgctt                                    30

<210> SEQ ID NO 21
<211> LENGTH: 30
<212> TYPE: DNA
<213> ORGANISM: Unknown
<220> FEATURE:
<223> OTHER INFORMATION: synthetic oligonucleotide

<400> SEQUENCE: 21
catggaattc gggctccccc gggagtatgt                                    30

<210> SEQ ID NO 22
<211> LENGTH: 21
<212> TYPE: DNA
<213> ORGANISM: Unknown
<220> FEATURE:
<223> OTHER INFORMATION: synthetic oligonucleotide

```
<400> SEQUENCE: 22
tagaaggcac cagtcgaggc t                                              21

<210> SEQ ID NO 23
<211> LENGTH: 69
<212> TYPE: DNA
<213> ORGANISM: Unknown
<220> FEATURE:
<223> OTHER INFORMATION: synthetic oligonucleotide

<400> SEQUENCE: 23
aattgcatca tcatcatcat cataatggtc ataccggtga acaaaaactc atctcagaag    60
aggatctgg                                                            69

<210> SEQ ID NO 24
<211> LENGTH: 69
<212> TYPE: DNA
<213> ORGANISM: Unknown
<220> FEATURE:
<223> OTHER INFORMATION: synthetic oligonucleotide

<400> SEQUENCE: 24
aattccagat cctcttctga gatgagtttt tgttcaccgg tatgaccatt atgatgatga    60
tgatgatgc                                                            69

<210> SEQ ID NO 25
<211> LENGTH: 30
<212> TYPE: DNA
<213> ORGANISM: Unknown
<220> FEATURE:
<223> OTHER INFORMATION: synthetic oligonucleotide

<400> SEQUENCE: 25
ccgggaattc gctggcattg gtgggcaggt                                     30

<210> SEQ ID NO 26
<211> LENGTH: 30
<212> TYPE: DNA
<213> ORGANISM: Unknown
<220> FEATURE:
<223> OTHER INFORMATION: synthetic oligonucleotide

<400> SEQUENCE: 26
ccgggaattc tttcaagatc tctgtgaggc                                     30

<210> SEQ ID NO 27
<211> LENGTH: 30
<212> TYPE: DNA
<213> ORGANISM: Unknown
<220> FEATURE:
<223> OTHER INFORMATION: synthetic oligonucleotide

<400> SEQUENCE: 27
ccgggaattc tggccccttg cagcgggcac                                     30

<210> SEQ ID NO 28
<211> LENGTH: 30
<212> TYPE: DNA
```

<213> ORGANISM: Unknown
<220> FEATURE:
<223> OTHER INFORMATION: synthetic oligonucleotide

<400> SEQUENCE: 28
ccgggaattc ggatcccacg tccgtagaaa    30

<210> SEQ ID NO 29
<211> LENGTH: 30
<212> TYPE: DNA
<213> ORGANISM: Unknown
<220> FEATURE:
<223> OTHER INFORMATION: synthetic oligonucleotide

<400> SEQUENCE: 29
ccgggaattc ggcagtgttg gaggctgggt    30

<210> SEQ ID NO 30
<211> LENGTH: 27
<212> TYPE: DNA
<213> ORGANISM: Unknown
<220> FEATURE:
<223> OTHER INFORMATION: synthetic oligonucleotide

<400> SEQUENCE: 30
ctaggaagct tgtttaactt gctagct    27

<210> SEQ ID NO 31
<211> LENGTH: 27
<212> TYPE: DNA
<213> ORGANISM: Unknown
<220> FEATURE:
<223> OTHER INFORMATION: synthetic oligonucleotide

<400> SEQUENCE: 31
agctagctag caagttaaac aagcttc    27

<210> SEQ ID NO 32
<211> LENGTH: 30
<212> TYPE: DNA
<213> ORGANISM: Unknown
<220> FEATURE:
<223> OTHER INFORMATION: synthetic oligonucleotide

<400> SEQUENCE: 32
catggctagc cgcaacgccc atctctgctt    30

<210> SEQ ID NO 33
<211> LENGTH: 30
<212> TYPE: DNA
<213> ORGANISM: Unknown
<220> FEATURE:
<223> OTHER INFORMATION: synthetic oligonucleotide

<400> SEQUENCE: 33
catggctagc ctcccccggg agtatgtgag    30

<210> SEQ ID NO 34
<211> LENGTH: 30
<212> TYPE: DNA
<213> ORGANISM: Unknown
<220> FEATURE:
<223> OTHER INFORMATION: synthetic oligonucleotide

<400> SEQUENCE: 34
catggctagc atggtggata gggccagtcc    30

```
<210> SEQ ID NO 35
<211> LENGTH: 30
<212> TYPE: DNA
<213> ORGANISM: Unknown
<220> FEATURE:
<223> OTHER INFORMATION: synthetic oligonucleotide

<400> SEQUENCE: 35
catggctagc agaccoctgc agtactcggc                                           30
```

The invention claimed is:

1. A method of treating or preventing p185$^{neu}$-positive tumors, metastases or tumor relapses, said method comprising intramusculary administering to a subject in need thereof a plasmid vector for DNA transfer, which plasmid contains the sequence of SEQ ID NO: 10 coding for a chimeric p185$^{neu}$-protein, or a pharmaceutical composition in the form of an injectable solution containing said plasmid vector together with pharmaceutically acceptable vehicles and excipients.

2. The method of claim 1 wherein said plasmid vector for DNA transfer further contains a transcription promoter.

3. The method of claim 2, wherein said promoter is the CMV promoter.

4. The method of claim 1, wherein said subject is a human subject.

5. The method of claim 1, wherein said pharmaceutical composition is suitable for parenteral administration.

6. The method of claim 5, wherein said pharmaceutical composition is in the form of an injectable solution.

7. The method of claim 1, wherein said pharmaceutical composition is a DNA vaccine.

8. The method of claim 2 wherein the p185$^{neu}$-positive tumors are p185$^{neu}$-positive primary tumors.

* * * * *